United States Patent
Sobek et al.

(10) Patent No.: US 7,429,468 B2
(45) Date of Patent: *Sep. 30, 2008

(54) MUTANT B-TYPE DNA POLYMERASES EXHIBITING IMPROVED PERFORMANCE IN PCR

(75) Inventors: Harald Sobek, Penzeberg (DE); Bruno Frey, Penzeberg (DE); Garabed Antranikian, Seevetal-Hittfeld (DE); Boehlke Kristina, Berlin (DE); Francesca Maria Pisani, Rome (IT); Mosè Rossi, Naples (IT)

(73) Assignee: Roche Diagnostics GmbH, Mannheim (DE)

( * ) Notice: Subject to any disclaimer, the term of this patent is extended or adjusted under 35 U.S.C. 154(b) by 410 days.

This patent is subject to a terminal disclaimer.

(21) Appl. No.: 11/077,886

(22) Filed: Mar. 11, 2005

(65) Prior Publication Data

US 2005/0266436 A1    Dec. 1, 2005

Related U.S. Application Data

(63) Continuation of application No. 09/803,165, filed on Mar. 9, 2001, now Pat. No. 6,881,559.

(30) Foreign Application Priority Data

Mar. 11, 2000   (EP)   ................... 00105155

(51) Int. Cl.
  *C12N 9/12*   (2006.01)
  *C12P 19/34*  (2006.01)
  *C12P 21/06*  (2006.01)
  *C07H 21/02*  (2006.01)
  *C07H 21/04*  (2006.01)

(52) U.S. Cl. .................. 435/91.2; 435/6; 435/69.1; 435/194; 435/199; 536/23.1; 536/23.2

(58) Field of Classification Search .............. 435/6, 435/91.1, 91.5, 455, 68.1, 69.1, 91.2, 91.4, 435/320.1, 252.3, 183, 91.51; 536/23.1, 536/23.2, 24.1

See application file for complete search history.

(56) References Cited

U.S. PATENT DOCUMENTS 6,881,559 B2 *  4/2005  Sobek et al. ............... 435/91.2

FOREIGN PATENT DOCUMENTS

DE   196 11 759 A1   3/1996

OTHER PUBLICATIONS

Anderson, W.F., "Human Gene Therapy," *Nature*, Apr. 1998, pp. 25-28, vol. 392.
Antranikian, G., et al., Accession DE19611759-A1, Apr. 1998.
Bohlke, K., et al., "PCR performance of the B-type DNA polymerase from the thermophilic euryachaeon *Thermococcus aggregans* improved by mutations in the Y-GG/A motif," *Nucleic Acids Research*, 2000, pp. 3910-3917, vol. 28, No. 20.
Bordo, D., et al., "Suggestions for "Safe" Residue Substitutions in Site-directed Mutagenesis," *J. Mol. Biol.*, 1991, pp. 721-729, vol. 217.
Niehaus, F., et al., "Cloning and characterization of a thermostable x-DNA polymerase from the hyperthermophilic archaeon *Thermococcus sp.* TY," *Gene*, 1997, pp. 153-158, vol. 204.
Pisani, F., et al., "Amino Acid Residues involved in Determining the Processivity of the 3'-5' Exonuclease Activity in a Family B DNA Polymerase from the Thermoacidophilic Archaeon *Sulfolobus solfataricus*," *Biochemistry*, 1998, pp. 15005-15012, vol. 37.
Truniger, V., et al., "Role of the 'YxGG/A' Motif of 029 DNA Polymerase in Protein-primed Replication," *J. Mol. Biol.* 1992, pp. 57-69, vol. 286.
Truniger, V., et al., "A DNA binding motif coordinating synthesis and degradation in proofreading DNA polymerases," *The Embo Journal*, pp. 3430-3441, vol. 15, No. 13, (1996).

* cited by examiner

*Primary Examiner*—Jane Zara
(74) *Attorney, Agent, or Firm*—Townsend and Townsend and Crew LLP

(57) ABSTRACT

The present invention relates to thermostable mutants of B-type DNA polymerases comprising a Y-GG/A amino acid motif between the N-terminal 3'-5'-exonuclease domain and the C-terminal polymerase domain whereas the tyrosine of the Y-GG/A amino acid motif is mutated and whereas these mutant DNA polymerases are suitable for PCR.

19 Claims, 11 Drawing Sheets

Figure 1

Figure 2:
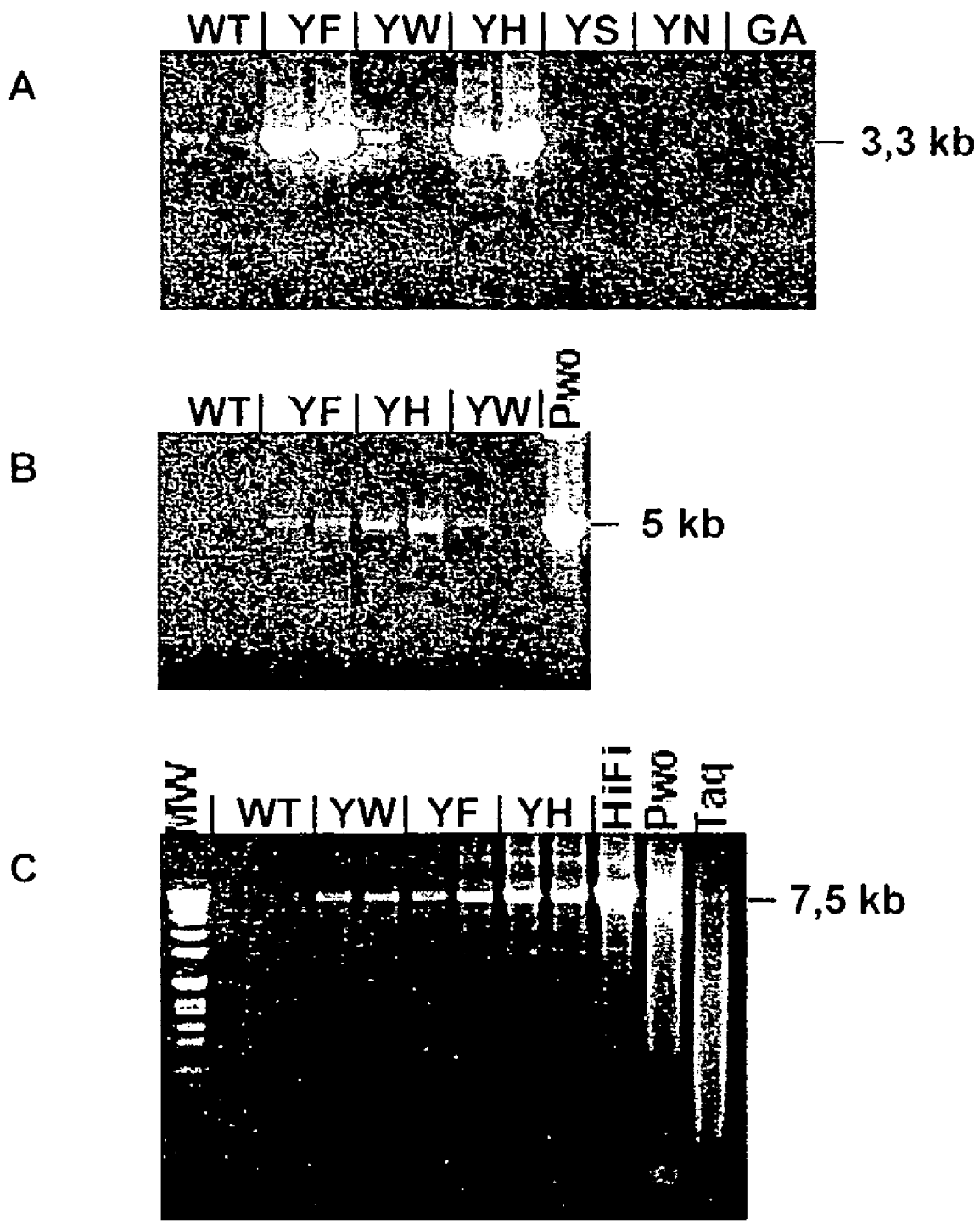

Pol activity and Exo activity in %

|  | WT | Y387F | Y387W | Y387H | Y387N | Y387S | G389A |
|---|---|---|---|---|---|---|---|
| Pol | 100 | 160 | 92 | 93,6 | 6,4 | 17,8 | 10,7 |
| Exo | 100 | 90 | 71 | 98 | 205 | 187 | 236 |
| Pol/Exo | 1 | 1,77 | 1,29 | 0,96 | 0,03 | 0,09 | 0,04 |

90 sec 40 sec 30 sec

|              | consensus | E |   | R R | R |   |   |   | G (Y) |   | K E |   | E |   | L W E |   |
|---|---|---|---|---|---|---|---|---|---|---|---|---|---|---|---|---|
| T. aggregans |   | E | Y | R R | L | R | T | T | Y | L | G G | Y | V | K E P E | R | G L W E | N |
| T. litoralis |   | E | Y | K R | R | L | R | T | T | Y | L G G | Y | V | K E P E | K | G L W E | N |
| T. fumicolans |   | E | L | E R | R | - | R | G | G | Y | A G G | Y | V | K E P E | R | G L W E | N |
| T. spec. 9N7 |   | E | L | A R | R | - | R | G | G | Y | A G G | Y | V | K E R E | R | G L W E | N |
| T. gorgonarius |   | E | L | A R | R | - | R | E | S | Y | A G G | Y | V | K E P E | R | G L W E | N | Euryarchaea
| P. spec. KOD |   | E | L | A R | R | - | R | Q | S | Y | E G G | Y | V | K E P E | R | G L W E | N |
| P. abysii |   | E | Y | E R | R | L | R | E | S | Y | E G G | Y | V | K E P E | K | G L W E | N |
| P. furiosus |   | E | Y | Q R | R | L | R | E | S | Y | T G G | F | V | K E P E | K | G L W E | N |
| P. horikoshii |   | E | Y | E R | R | L | R | E | S | Y | E G G | Y | V | K E P E | K | G L W E | N |
| M. jannaschii |   | E | Y | R R | R | V | L | T | T | Y | E G G | Y | V | K E P E | K | G W F E | D |
| M. voltae |   | S | Y | R E | R | A | K | F | S | Y | E G G | Y | V | R E P L | K | G I Q E | N |
| S. solfataricus |   | T | S | A L | I | K | G | K | G | Y | K G A | V | V | I D P P | A | G I F F | N |
| S. acidocaldarius |   | T | A | A V | I | K | G | K | K | Y | K G A | V | V | I D P P | A | G V Y F | N |
| P. islandicum |   | T | K | A I | I | K | G | K | K | Y | A G A | V | V | L D P P | L | G I F F | N | Crenarchaea
| P. occultum |   | S | E | A L | I | K | G | K | K | Y | Q G A | L | V | L D P P | S | G I Y F | N |
| A. pernix |   | V | G | A I | I | K | D | K | K | Y | R G A | I | V | L D P P | V | G I F F | R |
| S. chiwakuensis |   | T | A | A I | S | K | G | K | R | Y | K G A | V | V | I D P P | A | G V F F | N |

SEQ. ID. NO: 16

SEQ. ID. NO: 17

SEQ. ID. NO: 18

SEQ. ID. NO: 19

SEQ. ID. NO: 20

SEQ. ID. NO: 21

SEQ. ID. NO: 22

SEQ. ID. NO: 23

SEQ. ID. NO: 24

SEQ. ID. NO: 25

SEQ. ID. NO: 26

SEQ. ID. NO: 27

SEQ. ID. NO: 28

SEQ. ID. NO: 29

SEQ. ID. NO: 30

SEQ. ID. NO: 31

SEQ. ID. NO: 32

Figure 8

Figure 9/1

SEQ. ID. NO: 33
SEQ. ID. NO: 34

1/1
ATG ATA TTT GAC ACT GAC TAC ATA ACA AAG GAC GGT AAA CCC ATA ATT CGA ATT TTC AAG
Met ile phe asp thr asp tyr ile thr lys asp gly lys pro ile ile arg ile phe lys
61/21
AAA GAG AAC GGG GAA TTT AAA ATA GAA CTT GAT CCA CAT TTT CAG CCC TAC ATT TAC GCT
lys glu asn gly glu phe lys ile glu leu asp pro his phe gln pro tyr ile tyr ala
121/41
CTT CTC AAA GAT GAC TCC GCT ATT GAT GAA ATA AAA GCA ATA AAA GGC GAG AGA CAC GGA
leu leu lys asp asp ser ala ile asp glu ile lys ala ile lys gly glu arg his gly
181/61
AAA ATT GTG AGA GTA GTC GAT GCA GTG AAA GTC AAG AAG AAA TTT TTG GGG AGA GAT GTT
lys ile val arg val val asp ala val lys val lys lys lys phe leu gly arg asp val
241/81
GAG GTC TGG AAG CTT ATA TTT GAG CAT CCC CAA GAC GTC CCG GCC CTA AGG GGC AAG ATA
glu val trp lys leu ile phe glu his pro gln asp val pro ala leu arg gly lys ile
301/101
AGG GAA CAT CCA GCT GTG ATT GAC ATT TAT GAG TAC GAC ATA CCC TTT GCC AAG CGC TAC
arg glu his pro ala val ile asp ile tyr glu tyr asp ile pro phe ala lys arg tyr
361/121
CTC ATA GAC AAG GGC TTG ATC CCT ATG GAG GGC GAC GAG GAG CTT AAG CTA ATG GCC TTC
leu ile asp lys gly leu ile pro met glu gly asp glu glu leu lys leu met ala phe
421/141
GAC ATT GAG ACG TTT TAC CAC GAG GGA GAC GAG TTT GGG AAG GGC GAG ATA ATA ATG ATA
asp ile glu thr phe tyr his glu gly asp glu phe gly lys gly glu ile ile met ile
481/161
AGC TAC GCC GAT GAG GAA GAG GCA AGG GTA ATT ACA TGG AAG AAT ATT GAT CTG CCC TAC
ser tyr ala asp glu glu glu ala arg val ile thr trp lys asn ile asp leu pro tyr
541/181
GTT GAT GTT GTA TCC AAC GAA AGG GAG ATG ATA AAG CGG TTT GTG CAA ATT GTC AGG GAA
val asp val val ser asn glu arg glu met ile lys arg phe val gln ile val arg glu
601/201
AAA GAC CCG GAT GTC CTG ATA ACT TAC AAT GGA GAC AAC TTT GAT TTG CCG TAC CTT ATA
lys asp pro asp val leu ile thr tyr asn gly asp asn phe asp leu pro tyr leu ile
661/221
AAA AGG GCA GAG AAG TTA GGA GTT ACT CTT CTC TTG GGG AGG GAC AAA GAA CAC CCC GAG
lys arg ala glu lys leu gly val thr leu leu leu gly arg asp lys glu his pro glu
721/241
CCC AAG ATT CAC AGA ATG GGC GAT AGC TTT GCC GTG GAA ATT AAA GGC AGA ATT CAC TTT
pro lys ile his arg met gly asp ser phe ala val glu ile lys gly arg ile his phe
781/261
GAT CTC TTC CCG GTT GTG CGG AGA ACC ATA AAC CTC CCA ACA TAC ACG CTT GAG GCA GTT
asp leu phe pro val val arg arg thr ile asn leu pro thr tyr thr leu glu ala val
841/281
TAT GAA GCC GTC TTG GGA AAA ACC AAA AGC AAG CTG GGT GCG GAG GAA ATC GCC GCC ATC
tyr glu ala val leu gly lys thr lys ser lys leu gly ala glu glu ile ala ala ile
901/301
TGG GAA ACA GAG GAG AGC ATG AAG AAG CTG GCC CAG TAC TCG ATG GAA GAT GCT AGG GCA
trp glu thr glu glu ser met lys lys leu ala gln tyr ser met glu asp ala arg ala
961/321
ACT TAT GAA CTC GGA AAA GAG TTT TTC CCC ATG GAG GCA GAG CTA GCA AAG CTA ATA GGC
thr tyr glu leu gly lys glu phe phe pro met glu ala glu leu ala lys leu ile gly
1021/341
CAA AGC GTA TGG GAC GTC TCA AGA TCA AGC ACT GGC AAC CTT GTA GAG TGG TAC CTG TTA
gln ser val trp asp val ser arg ser ser thr gly asn leu val glu trp tyr leu leu
1081/361

Figure 9/2

SEQ. ID. NO: 33
SEQ. ID. NO: 34

```
AGG GTG GCA TAT GAG AGG AAT GAG CTC GCT CCG AAC AAG CCG GAT GAA GAA GAG TAC AGA
arg val ala tyr glu arg asn glu leu ala pro asn lys pro asp glu glu glu tyr arg
1141/381
AGG CGT TTA AGG ACT ACT TAC CTG GGA GGA TAC GTA AAA GAG CCG GAA AGA GGC TTA TGG
arg arg leu arg thr thr tyr leu gly gly tyr val lys glu pro glu arg gly leu trp
1201/401
GAG AAC ATC ACC TAT TTA GAC TTT AGG TGC CTA TAC CCC TCA ATT ATA GTT ACC CAC AAC
glu asn ile thr tyr leu asp phe arg cys leu tyr pro ser ile ile val thr his asn
1261/421
GTC TCC CCT GAC ACT TTA GAA AGA GAA GGC TGC AAG AAT TAC GAT GTT GCC CCG ATA GTA
val ser pro asp thr leu glu arg glu gly cys lys asn tyr asp val ala pro ile val
1321/441
GGT TAT AAG TTC TGC AAG GAT TTT CCC GGT TTC ATT CCA TCT ATA CTC GGG GAA TTA ATC
gly tyr lys phe cys lys asp phe pro gly phe ile pro ser ile leu gly glu leu ile
1381/461
ACA ATG AGG CAA GAA ATA AAG AAG AAG ATG AAA GCT ACA ATT GAC CCA ATA GAA AAG AAA
thr met arg gln glu ile lys lys lys met lys ala thr ile asp pro ile glu lys lys
1441/481
ATG CTT GAT TAT AGG CAA AGA GCT GTT AAA TTG CAC GCA AAC AGC TAT TAC GGT TAT ATG
met leu asp tyr arg gln arg ala val lys leu his ala asn ser tyr tyr gly tyr met
1501/501
GGC TAT CCC AAG GCG AGG TGG TAC TCG AAG GAA TGT GCC GAA AGC GTT ACC GCG TGG GGA
gly tyr pro lys ala arg trp tyr ser lys glu cys ala glu ser val thr ala trp gly
1561/521
AGG CAC TAC ATA GAA ATG ACC ATA AAA GAG ATA GAG GAG AAA TTT GGA TTT AAG GTG CTA
arg his tyr ile glu met thr ile lys glu ile glu glu lys phe gly phe lys val leu
1621/541
TAT GCC GAC ACT GAT GGT TTT TAC GCC ACA ATA CCG GGA GAA AAA CCT GAA ACA ATC AAA
tyr ala asp thr asp gly phe tyr ala thr ile pro gly glu lys pro glu thr ile lys
1681/561
AAG AAA GCT AAG GAA TTC TTA AAA TAC ATA AAC TCC AAA CTT CCC GGT CTG CTC GAG CTT
lys lys ala lys glu phe leu lys tyr ile asn ser lys leu pro gly leu leu glu leu
1741/581
GAG TAT GAG GGC TTT TAC TTG AGA GGA TTT TTC GTC GCA AAG AAG CGC TAT GCG GTT ATA
glu tyr glu gly phe tyr leu arg gly phe phe val ala lys lys arg tyr ala val ile
1801/601
GAC GAA GAA GGT AGG ATA ACG ACA AGG GGT CTG GAA GTT GTA AGG AGG GAC TGG AGC GAA
asp glu glu gly arg ile thr thr arg gly leu glu val val arg arg asp trp ser glu
1861/621
ATA GCC AAA GAG ACC CAG GCT AAA GTC TTG GAG GCA ATA CTT AAA GAA GAT AGT GTC GAA
ile ala lys glu thr gln ala lys val leu glu ala ile leu lys glu asp ser val glu
1921/641
AAA GCT GTG GAA ATC GTT AAG GAC GTT GTT GAG GAG ATA GCA AAA TAC CAA GTC CCG CTT
lys ala val glu ile val lys asp val val glu glu ile ala lys tyr gln val pro leu
1981/661
GAA AAG CTT GTT ATC CAC GAG CAG ATT ACC AAG GAT CTA AGT GAA TAC AAA GCC ATT GGG
glu lys leu val ile his glu gln ile thr lys asp leu ser glu tyr lys ala ile gly
2041/681
CCT CAT GTA GCA ATA GCA AAG AGG CTT GCT GCA AAG GGA ATA AAA GTG AGA CCC GGC ACG
pro his val ala ile ala lys arg leu ala ala lys gly ile lys val arg pro gly thr
2101/701
ATA ATA AGC TAT ATC GTC CTC AGG GGA AGC GGA AAG ATA AGT GAC AGG GTA ATT TTG CTT
ile ile ser tyr ile val leu arg gly ser gly lys ile ser asp arg val ile leu leu
2161/721
```

Figure 9/3

SEQ. ID. NO: 33
SEQ. ID. NO: 34

```
TCA GAG TAT GAT CCG AAA AAA CAC AAG TAC GAC CCC GAC TAC TAC ATA GAA AAC CAA GTT
ser glu tyr asp pro lys lys his lys tyr asp pro asp tyr tyr ile glu asn gln val
2221/741
CTG CCG GCG GTG CTT AGG ATC CTT GAA GCC TTC GGC TAC AGA AAA GAG GAC TTA AAA TAC
leu pro ala val leu arg ile leu glu ala phe gly tyr arg lys glu asp leu lys tyr
2281/761
CAA AGC TCA AAA CAG GTT GGA CTG GAC GCG TGG CTT AAG AAG TAG
gln ser ser lys gln val gly leu asp ala trp leu lys lys AMB
```

MUTANT B-TYPE DNA POLYMERASES EXHIBITING IMPROVED PERFORMANCE IN PCR

The present application is a continuation of U.S. patent application Ser. No. 09/803,165, filed on Mar. 9, 2001, which claims priority to European Patent Application No. 00105155.6, filed Mar. 11, 2000, each of which are incorporated by reference in their entirety.

FIELD OF THE INVENTION

Subject of the invention is a thermostable mutant B-type DNA-polymerase having a Y-GG/A amino acid motif between the N-terminal 3'-5'-exonuclease domain and the C-terminal polymerase domain in the wild type form whereas amino acids of this motif are substituted in the mutant form of the DNA polymerase and whereas these mutant DNA polymerases are suitable for PCR reactions. Thermostable mutants according to the present invention exhibit better performance in PCR reactions compared to the wild type DNA polymerase. A further embodiment of the present invention is the use of these thermostable mutants of the B-type DNA polymerase for polymerase chain reactions (PCR) and other nucleic acid synthesizing reactions. Another subject of the present invention is a method of producing the inventive mutants, vectors and cell lines comprising genes encoding the inventive mutants.

BACKGROUND OF THE INVENTION

DNA-dependent DNA polymerases containing proofreading activity have to coordinate two catalytic activities: the DNA polymerase activity and the exonuclease activity. For polymerase I type DNA polymerases (*E. coli* Pol I) as well as for B-type DNA polymerases, these catalytic activities are located on structurally distinct protein domains (Truniger, V., Lázaro, J., Salas, M. and Blanco, L. (1996) *EMBO J.*, 15(13), 3430-3441; Pisani, F. M., De Felice, M. and Rossi, M. (1998) *Biochemistry*, 37(42), 15005-15012). In B-type (eukaryotic-type) DNA polymerases, the coordination of the two catalytic activities was proposed to take place intramolecularly in the conserved motif Y-GG/A located between the N-terminal 3'-5' exonuclease and the C-terminal polymerization domain (Truniger, V., Lázaro, J., Salas, M. and Blanco, L. (1996) *EMBO J.*, 15(13), 3430-3441; Pisani, F. M., De Felice, M. and Rossi, M. (1998) *Biochemistry*, 37(42), 15005-15012). For the Klenow fragment of *E. coli* DNA polymerase it was described, that the editing can be an intermolecular or intramolecular process involving dissociation and reassociation of the DNA depending on the local context (Joyce, C. M. (1989) *JBC*, 264(18), 10858-10866). Truniger et al. (Truniger, V., Lázaro, J., Salas, M. and Blanco, L. (1996) *EMBO J.*, 15(13), 3430-3441) demonstrated for the mesophile replicative DNA polymerase of bacteriophage φ29 that mutations in the Y-GG/A motif can lead to phenotypes favoring either polymerisation or exonucleolysis compared to the wild type enzyme. They could show that this effect is related to altered (ss)DNA binding parameters and that the motif is important for the communication between the polymerase and exonuclease active site in a combination of structural and functional roles.

For the DNA polymerase of the thermophilic crenarchaeon *Sulfolobus solfataricus* (Sso) a region of 70 amino acids (region 1) involved in enzyme-DNA interaction was determined (Pisani, F. M., Manco, G., Carratore, V. and Rossi, M. (1996) *Biochemistry*, 35, 9158-9166). It is located in the connecting part between the exonuclease domain and the polymerase domain and contains the Y-GG/A motif. By mutational analysis of the amino acids in the Y-GG/A motif, it could be shown that the amino acids in this part of the enzyme determine the processivity of the proofreading function (Pisani, F. M., De Felice, M. and Rossi, M. (1998) *Biochemistry*, 37(42), 15005-15012). Based on the crystal structure of bacteriophage RB69 DNA polymerase, Truniger et al. proposed a direct interaction of the tyrosine with the phosphodiester bond between the two nucleotides preceding the one acting as template (Truniger, V., Blanco, L. and Salas, M. (1999) *J. Mol. Biol.*, 286, 57-69).

DESCRIPTION OF THE INVENTION

The subject of the present invention was to provide thermostable DNA polymerases exhibiting an improved performance in PCR. Especially, thermostable mutants of a B-type DNA polymerase are provided which exhibit improved PCR performance. The inventive mutants of the B-type DNA polymerase have mutations in the Y-GG/A amino acid motif. Preferred mutations refer to the position of the tyrosine in the Y-GG/A amino acid motif. Other mutations affecting the motif could also influence the performance of B-type DNA polymerases in PCR.

According to the present invention an improved performance of a DNA polymerase in PCR is defined as a performance that results in higher yields of PCR product, or the amplification of longer DNA targets. Additionally, improved PCR performance can be defined as improved fidelity during the amplification process.

Preferred mutant B-type DNA polymerases have mutations at the position of the tyrosine in the Y-GG/A amino acid motif. Preferred mutants of B-type DNA polymerases according to the present invention have phenylalanine, tryptophan or histidine at the position of the tyrosine. Other preferred mutants of B-type DNA polymerases according to the present invention have asparagine or serine at the position of the tyrosine. These mutant polymerases described here, in which the tyrosine of the Y-GG/A motif was substituted, exhibit an improved performance in In a preferred embodiment the inventive mutant B-type DNA polymerase is a mutant of a B-type DNA polymerase obtainable from Euryarchaea, more preferably from *Thermococcus aggregans* (Tag). Especially preferred is a mutant of a B-type DNA polymerase from Tag of about 94 kDa size with a temperature optimum of ≧80° C. and the ability to perform polymerase chain reactions The present invention is described in detail for the B-type DNA polymerase from *Thermococcus aggregans*, but the invention could also be applied to other B-type DNA polymerases. Preferrably to those B-type DNA polymerases showing a high degree of homology (≧80%) to the DNA polymerase from *Thermococcus aggregans*.

The B-type DNA polymerase from *Thermococcus aggregans* exhibits a high degree of amino acid sequence homology to B-type DNA polymerases of other *Thermococcus* species. The homology of the DNA polymerases was calculated using the programm Blast 2 (Tatusova, T. A. and Madden, T. L. (1999) *FEMS Microbiol. Lett.* 174, 247-250). The homology of the B-type DNA polymerase from *Thermococcus aggregans* to the homologue enzymes from *Thermococcus* species is: 93% (*T. litoralis*), 87% (*T. gorgonarius*), 86% (*T. furiosus*) and 87% (T. spec. 9N7). The homology of the Tag DNA polymerase to polymerases from *Pyrococcus* species is: 86% (*P. abysii*), 86% (*P. horikoshii*), 86% (P. spec KOD) and 85% (*P. furiosus*). A lower homology is calculated to other B-type DNA polymerase from different euryarchaeota: 59% (*Methanococcus jannaschii*), 56% (*Methanococcus voltae*), 51% (*Methanobacterium thermoautotrophicum*) and 56% (*Archaeglobus fulgidus*). To B-type DNA polymerases from crenarchaeota and bacteriophages the homology is found as follows: 46% (*Sulfolobus solfataricus*), 42% (*Sulfolobus acidocaldarius*), 41% (*Sulfurisphera ohwakuensis*), 51% (*Aeropyrum pernix*), 40% (*Pyrodictium occultum*), 43% (*Cenarchaeum symbiosum*), 38% (bacteriophage T4) and 39% (bacteriophage RB69).

As described above several mutations in the Y-GG/A motif were performed for the *Sulfolobus solfataricus* (Sso) and the φ29 DNA polymerases. The observed effects on polymerase activity (pol) and exonuclease activity (exo) of these mutations do not completely correspond to the effects obtained for the Tag DNA polymerase. Thus the effect of the mutations on the performance of the mutants in PCR was not predictable.

The mutant Y387F of the Tag DNA polymerase exhibits a higher pol/exo ratio compared to the wild type Tag DNA polymerase. Similar results were described for Sso and φ29 DNA polymerase. The mutant G389A displays the opposite effect than the corresponding mutant in φ29 DNA polymerase: while G→A in Tag DNA polymerase almost knocks out polymerase-activity, in φ29 DNA polymerase G→A mutant this activity is clearly enhanced. For mutants of the Sso DNA polymerase a change of exonuclease processivity was described. Again, this was not observed for mutants of the B-type Tag DNA polymerases. Thus, a prediction of the effect of analogous mutants in the Y-GG/A motif could not be made.

In summary, although it has been described in the prior art that the Y-GG/A motif plays a role in the coordination of the DNA polymerase activity and the exonuclease activity, the observed changes of the pol/exo ratio of the prior art DNA polymerases do not strictly correlate to the changes observed for the inventive mutants of the Tag DNA polymerase. Furthermore, it has not been described that the Y-GG/A motif is important for the performance of B-type DNA polymerase in PCR. Additionally, there is no correlation between the changes of the pol/exo ratio and the improvement of the performance of DNA polymerases in PCR. For instance, the mutant Y387H does not exhibit a change of pol/exo ratio compared to the wild-type, but it exhibits improved performance in PCR. Furthermore, a significant enhancement of fidelity was observed for the mutants Y387N and Y387S of Tag DNA polymerase.

Results obtained for the mutants of Tag DNA polymerase are described in more detail below.

Enzymatic Activities of Wild Type and Mutant Tag DNA Polymerases

The enzymatic activities of the wild type enzyme and the mutants of Tag DNA polymerase were determined and analyzed (FIG. 1). The DNA polymerase activity was determined as described in Example 2. According to the effect of the mutations on the polymerase activity three groups of mutants were defined: i) mutants with enhanced DNA polymerase activity (mutant Y387F), ii) mutants having a similar or slightly reduced DNA polymerase activity compared to the wild type (mutants Y387W and Y387H) and iii) mutants with reduced DNA polymerase activity (mutants Y387N, Y387S, G389A).

The exonuclease activity was determined as described in Example 3. According to the effect of the mutations on the exonuclease activity two groups of mutants were defined: i) mutants with similar exonucleolytic activity as the wild type enzyme (mutants Y387F, Y387W, Y387H), ii) mutants with enhanced exonuclease activity (mutants Y387N, Y387S, G389A) in comparison to the wild type enzyme.

From the data obtained for polymerase activity and exonuclease activity the ratios of both activities (pol/exo) were calculated for the wild type enzyme and the mutants of Tag DNA polymerase (FIG. 1). Three mutants showed a higher or similar pol/exo ratio as the wild type enzyme (mutants Y387F, Y387W, Y387H). Three mutants showed a clearly reduced pol/exo ratio in comparison to the wild type enzyme (mutants Y387N, Y387S, G389A).

PCR Performance

Wild type and mutant enzymes were submitted to polymerase chain reactions on lambda DNA in a buffer optimized for this purpose. All mutants except for mutant G389A were able to perform PCR, but yielded different amounts of product with a constant amount of enzyme (1 pmol). With increasing length of the DNA target, differences in performance of the enzyme were shown (FIG. 2). With 1 pmol of the mutants Y387S, Y387N and G389A no PCR product could be obtained for the amplification of a 3.3 kb fragment. 1 pmol of the wild type DNA polymerase could not amplify fragments of 5.0 kb length. The mutants Y387W, Y387F and Y387H were able to amplify a fragment of 7.5 kb length. As control Taq DNA polymerase, Pwo DNA polymerase and Expand™ High Fidelity PCR System (Roche Molecular Biochemicals) were used.

Figure 3:
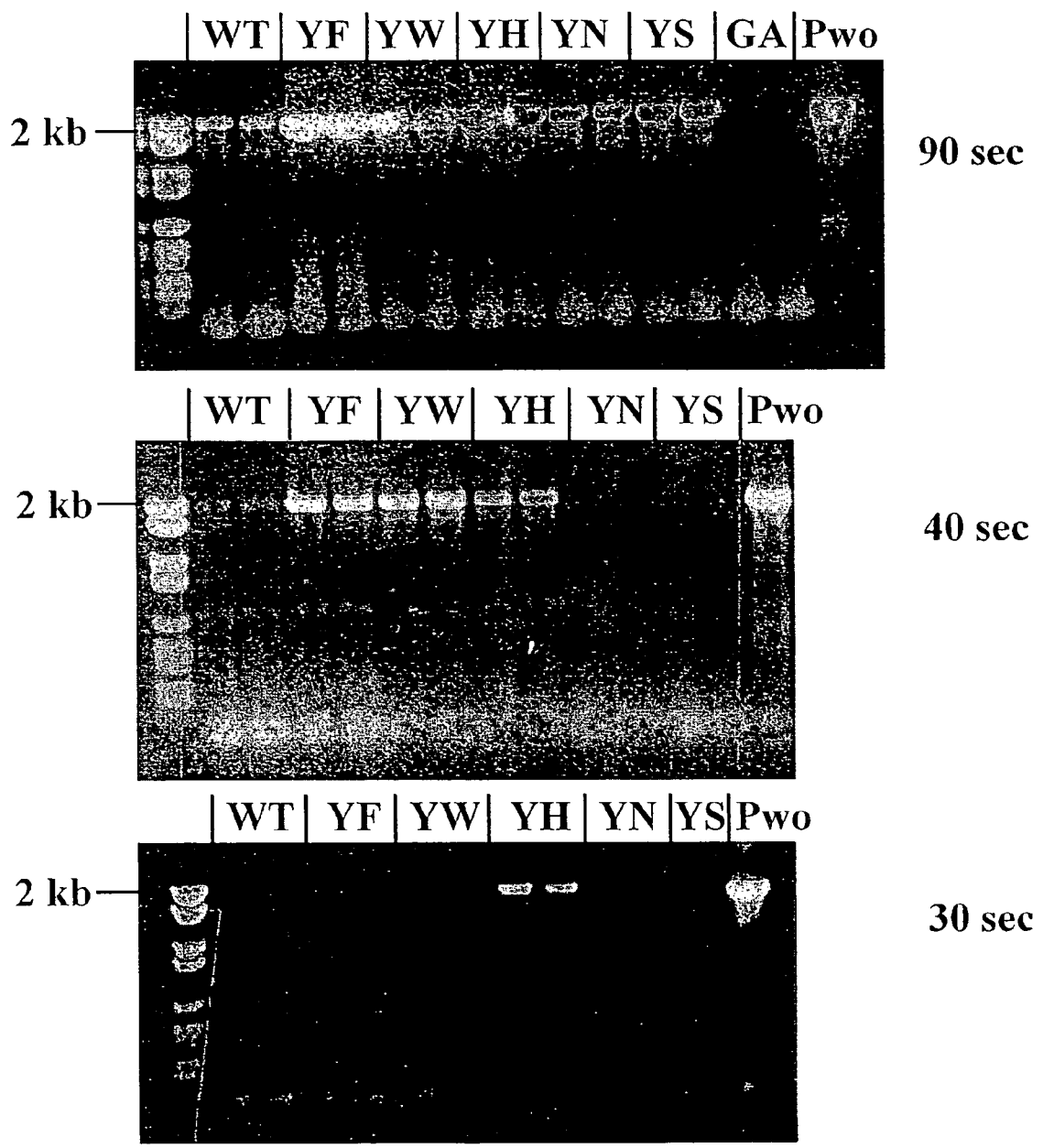

The differences in PCR performance were also shown by the amplification of a 2 kb fragment applying different elongation times in the PCR runs. Under these conditions, all enzymes tested except the mutant G389A were able to amplify a 2 kb fragment at an elongation time of 90 sec/cycle. The mutants Y387F, Y387W and Y387H were able to amplify the fragment at a reduced elongation time of 40 sec/cycle. The mutant Y387H was able to amplify the target in a elongation time of 30 sec/cycle (FIG. 3).

Exonuclease Processivity

Figure 4:
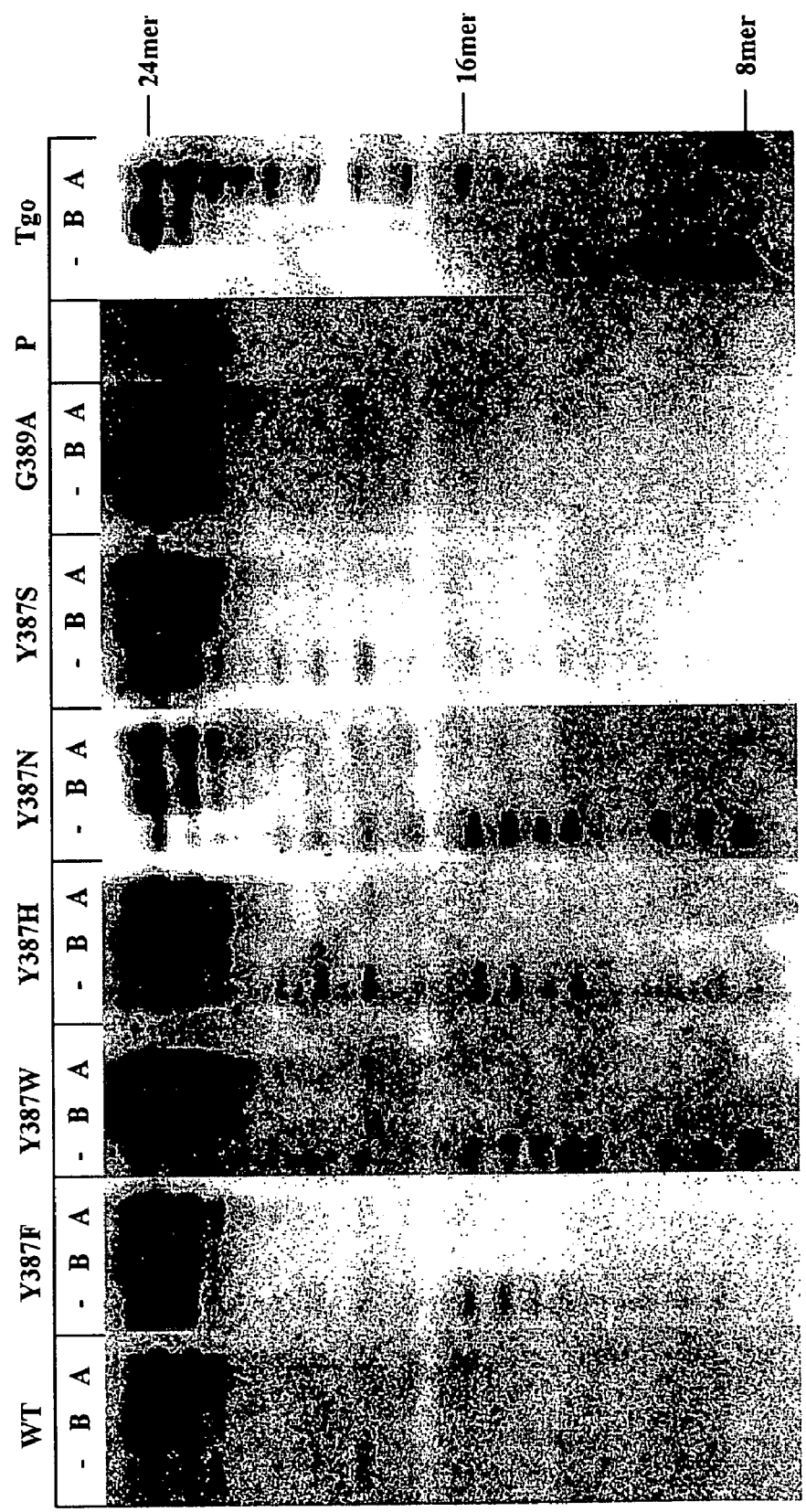

The exonuclease processivity of the enzymes was studied in an experiment based on the heparin trap method (Reddy, M. K., Weitzel, S. E. and von Hippel, P. H. (1992) *J. Biol. Chem.*, 267(20), 14157-14166; Pisani, F. M., De Felice, M. and Rossi, M. (1998) *Biochemistry*, 37(42), 15005-15012). A constant amount (1 pmol) of Tag DNA polymerase or its mutants was incubated for 4 minutes at 68° C. with a 5'-DIG-labelled 24mer oligonucleotide in the absence of nucleotides. In the absence of heparin, the oligonucleotide was continually degraded by the Tag enzymes (positive control, FIG. 4, lanes "-"). The function of the heparin trap method was demonstrated by addition of heparin and $MnCl_2$ before the binding of the enzyme (negative control, FIG. 4, lanes B). Single turnover conditions (addition of heparin and $MnCl_2$ to start the reaction after the binding of enzyme) resulted in exonucleolytic degradation of the oligonucleotide by the Tag DNA polymerases (FIG. 4, lanes A). The enzymes showed differences in the exonucleolytic activity as shown by the different amounts of remaining oligonucleotide that was not degraded. However, for all enzymes tested the oligonucleotide was degraded to a similar extent (8 nt). This indicates a similar exonuclease processivity for the enzymes.

The *Thermococcus gorgonarius* DNA polymerase, which exhibits a strong exonuclease activity, was used as a positive control. It degraded the 24mer oligonucleotide in the absence of heparin to oligonucleotides of less than 15 bases length (FIG. 4, lane "-"). Under single turnover conditions a strong degradation (11 nt) of the oligonucleotide is observed (FIG. 4, lane "A").

Fidelity

The error rates in amplification were determined for the mutant enzymes and the wild type DNA polymerase. The PCR-based fidelity assay described by Frey and Suppman (Frey, M. and Suppmann, B. (1995) *Biochemica*, 2, 34-35) was used. This method is based on the amplification, circulation and transformation of the pUC19 derivative pUCQ17, which contains a functional lacI$^q$ allele (Barnes, W. M. (1994) *Proc. Natl. Acad. Sci. USA*, 91, 2216-2220). PCR-derived mutations in lacI result in a de-repression of the expression of lacZα and subsequent formation of a functional β-galactosidase enzyme, which can be detected on X-Gal indicator plates.

In five independent runs, a mean error rate of $5.0 \times 10^{-6}$ was found for the wild type Taq DNA polymerase. This value is in between the mean error rates of $1.8 \times 10^{-6}$ for Expand™High Fidelity PCR System (Roche Molecular Biochemicals) and $1.3 \times 10^{-5}$ for Taq DNA polymerase (Roche Molecular Biochemicals) determined in the corresponding experiments. For a better comparison of the data, we plotted the quotient of the error rate determined for Taq DNA polymerase divided by the error rates determined for the Tag DNA polymerase and its mutants. In the independent experiments the error rate for Taq DNA polymerase varied from 1.2 to $3.05 \times 10^{-5}$.

Figure 5:
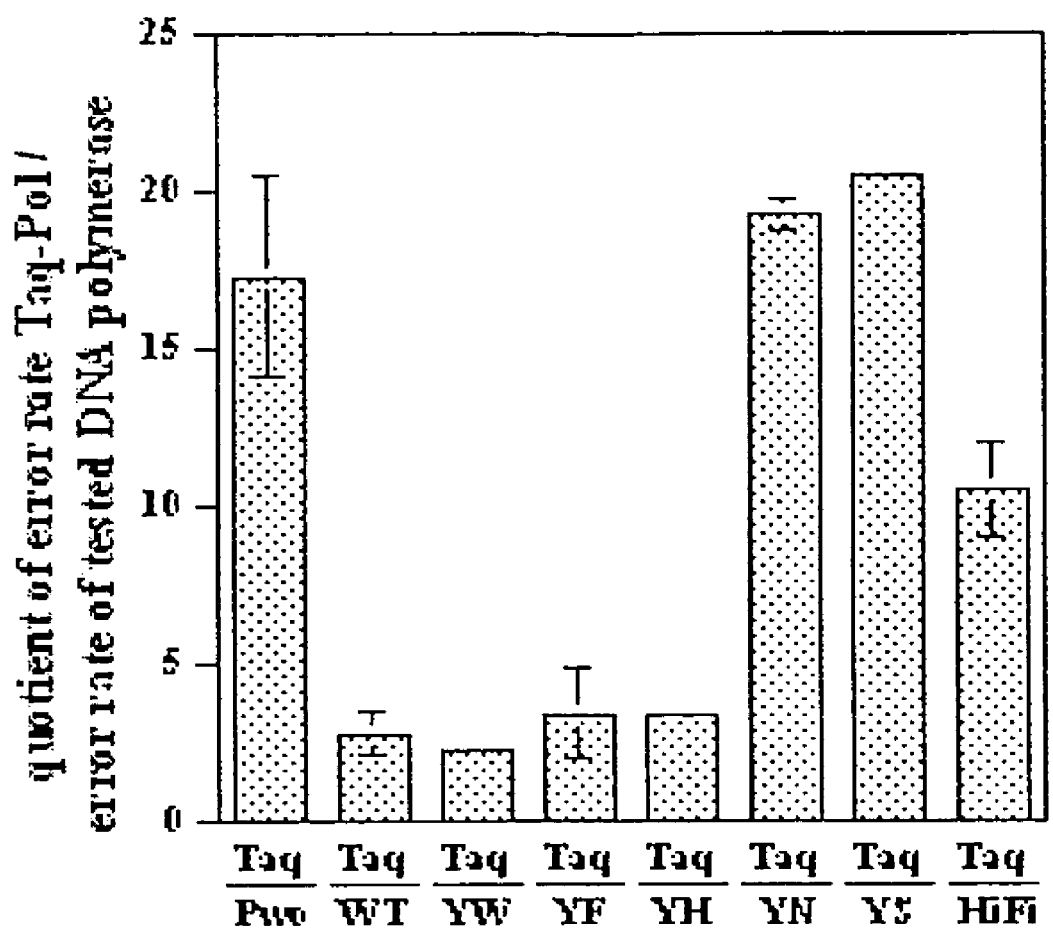

FIG. 5 shows the quotients of the error rates of the wild type enzyme and mutants of Tag DNA polymerase. The error rates of the mutants showing improved PCR performance (Y387W, Y387F, Y387H) did not significantly differ from the values obtained for the wild type enzyme. The mutants with enhanced exonuclease activity (Y387N, Y387S) showed improved fidelity rates (FIG. 5). For the mutants Y387N and Y387S mean error rates of $6.3 \times 10^{-7}$ and $6.2 \times 10^{-7}$ were determined.

In contrast to the φ29 DNA polymerase and the Sso DNA polymerase, the Tag DNA polymerase, is suited for PCR. The mutant enzymes (Y387F, Y387W, Y387H) with an aromatic amino acid in the position of the tyrosine showed a similar or only slightly enhanced DNA polymerase activity (mutants Y387F, Y387W, Y387H) but an improvement in PCR performance.

In the fidelity assay it was found that the mutants Y387F; Y387W and Y387H showed no significant change in their error rate. By contrast, the mutants Y387N or Y387S showed higher exonuclease activity and displayed an improved fidelity.

Subject of the present invention is also a method of producing the inventive B-type mutants comprising the following steps: cloning and mutagenesis of the gene, followed by the expression and purification of the protein.

Subject of the present invention is a DNA encoding for a thermostable B-type DNA polymerase having a Y-GG/A amino acid motif between the N-terminal 3'-5' exonuclease domain and the C-terminal polymerase domain in the wild type enzyme whereas the tyrosine of this motif is substituted in the mutant enzyme of the polymerase and whereas this mutant DNA polymerase is suitable for PCR.

Preferably, said DNA in wild type form is obtainable from Euryarchaea, more preferably from *Thermococcus aggregans* (Tag). Subject of the present invention is also a vector containing the inventive DNA. Suitable vectors are e.g. the following: pET14b/15b/16b/19b (Novagen); pRSET (Invitrogen); pTrcHis (Invitrogen); pHAT10/11/12 (Clontech); pPRO Tet.E/Lar.A (Clontech); pCALn/n-EK (Stratagene); pGEMEX-1/-2 (Promega).

Furthermore, subjects of the present invention are also cells comprising the above vector. Suitable cells are e.g. *E. coli* BL21, BL21(DE3), BL21(DE3)pLysS, BL21(DE3)pLysE, DH5αPRO, JM109 (DE3), TOP10 in combination with the vectors recommended by the suppliers. The gene may have to be subdoned and the protein purification procedure may have to be adapted in the case of different expression vectors.

A sample of the recombinant strain expressing Tag DNA polymerase was deposited with the Deutsche Sammlung von Mikroorganismen und Zellkulturen (DSMZ) Mascheroder Weg 1b, D-38124 Braunschweig (DSM No. 13224).

A further subject of the invention is the use of the inventive mutant enzymes for synthesizing nucleic acids e.g. in PCR reactions.

DETAILED DESCRIPTION OF THE PREFERRED EMBODIMENTS

Figures:
FIG. 1.

Table showing the relative polymerase activities (Pol) and 3'-5'-exonuclease activities (Exo) of Tag DNA polymerase and its mutants on double-stranded DNA.

Assays were carried out as described in example 2 and 3, respectively. The activities are expressed as percentage of the activity obtained for the wild-type Tag DNA polymerase.

FIG. 2.

PCR with Tag DNA Polymerase Mutants.

Tag DNA polymerase mutants (1 pmol) were incubated in a 50 µl total volume with 10 ng of lambda DNA as template and 30 pmoles of a primer set designed to yield the indicated fragment lengths, 200 µM dNTPs and the suitable PCR buffer. Reactions were performed with 10 cycles of 10 sec 94° C., 30 sec 57° C. and 3.0 min (A), 4.3 min (B) or 7.0 (C) min of elongation time at 72° C. followed by 20 cycles with elongation times increasing by 20 sec/cycle. After the PCR 5 µl sample were submitted to electrophoresis on a 1% agarose gel. For the control reaction 2.5 U of Taq DNA polymerase, Pwo DNA polymerase or Expand™ High Fidelity PCR System were used. The labeling of the lanes is described in the legend of FIG. 6.

FIG. 3.

Time-Dependent Polymerase Chain Reaction.

1% agarose gels showing 2 kb PCR products from reactions performed with different elongation time (90 sec, 40 sec, 30 sec as indicated) to determine the minimal elongation time.

1 pmol of each Tag DNA polymerase mutant or wild type enzyme was added to a mix of 10 ng lambda DNA and primers designed to yield 2 kb DNA fragments. Labeling of the lanes is described in the legend of FIG. 6. For each mutant duplicate reactions were performed. Right lane of each gel Pwo: 2.5 U *Pyrococcus woesei* DNA polymerase (Roche Molecular Biochemicals) as control reaction. Left lane of each gel: Molecular weight marker VI (Roche Molecular Biochemicals). In the 40 sec reaction, mutant GA was omitted. In the 30 sec reaction, for the mutant YS only one reaction was run on the gel.

FIG. 4.

3'-5'-exonuclease Processivity.

The Tag DNA polymerase mutants tested are indicated on top of the figure. Tgo DNA polymerase was used as a control reaction (incubation for 30 sec). Reactions for wild type and mutants of Tag DNA polymerase were performed for 4 minutes at 68° C. after preincubation for 1 minute at 68° C. Lane "P" is the control reaction (24 mer 5'-DIG-labelled primer without incubation), lane "-":reaction without heparin (positive control); lane "B": reaction with heparin and $MnCl_2$ added before addition of the enzyme (negative control); lane "A": heparin and $MnCl_2$ added after the enzyme (reaction under single turnover conditions).

FIG. 5.

Fidelity of Tag DNA Polymerase Mutants.

The fidelity of Tag DNA polymerase and its mutants was expressed in relation to the fidelity of Taq DNA polymerase. A quotient of 1 means that the polymerase has the same error rate as Taq DNA polymerase (mean value $1.3 \times 10^{-5}$). Values>1 reflect the factor by which a polymerase shows less errors than Taq DNA polymerase. The bars correspond to to mean values calculated from 2-5 independent experiments, error bars missing are smaller than 0.36. Abbreviations for enzymes are as indicated in legend to FIG. 6. As controls *Pyrococcus woesei* DNA polymerase (Roche Molecular Biochemicals) and Expand High Fidelity PCR System (Roche Molecular Biochemicals) were used ("Taq/Pwo" and "Taq/HiFi").

FIG. 6.

SDS-PAGE Gel Analysis of Purified Mutant Proteins.

1 µg of each mutant was submitted to electrophoresis on an 10% SDS-PAGE gel. Left: MW, molecular weight marker; W, *Thermococcus aggregans* wild type DNA polymerase; YF, YW, YS, YN, YH are the corresponding mutants with an exchange at the position of tyrosine 387 to phenylalanine, tryptophan, serine, asparagine, histidine, respectively. GA, mutation of glycine 389 to alanine in the gene of the *Thermococcus aggregans* DNA polymerase. All mutants showed the same chromatographic behaviour and solubility as the wild type enzyme.

FIG. 7.

Qualitative Exonuclease Assay.

A DNA molecular weight marker was used as substrate to test the exonucleolytic activity (DNA molecular weight marker II (MW II), Roche Molecular Biochemicals). 1 µg of MW II was incubated for 6 h at 65° C. with 1 pmol of each variant of Tag DNA polymerase in the presence (A) or absence (B) of 200 µM dNTP. Tag mutants are named as explained in legend of FIG. 6. Exonucleolytic degradation take place only in the absence of deoxynucleotides. The qualitative ranking of the proteins in terms of exonuclease activity is GA>YN>YS>YH>YF=YW=WT.

FIG. 8.

Consensus sequence motif for B-type DNA polymetases from the order of *Thermococcales* derived from a multiple alignment of amino acid sequences of euryarchaeal and crenarchaeal B-type DNA polymerases.

A region of 24 amino acids containing the Y-GG/A motif was analyzed with the ClustalW Software program (Higgins, EMBL Heidelberg, Germany). In addition to the amino acids conserved in all archaeal B-type DNA polymerases (like the Y-GG/A motif), a consensus sequence "E--RR-R-----G(Y)-KE-EE--LWE-" (SEQ ID NO:35) can be defined. This sequence is found in the sequence of all DNA polymerases belonging to the order of the *Thermococcales* and coincides with a homology of >80% of the DNA polymerases.

The sequences of the crenarchaeal species *Sulfolobus solfataricus, Sulfolobus acidocaldarius, Pyrobaculum islandicum, Pyrodictium occultum, Aeropyrum pernix, Sulfurisphaera ohwakuensis* and the sequences of several euryarchaeal species *Thermococcus* ("T."), *Pyrococcus* ("P.") and *Methanococcus* ("M.") were aligned.

FIG. 9.

DNA Sequence and Deduced Amino Acid Sequence of Recombinant Wild Type Tag DNA Polymerase.

Three inteins found in the native gene (Acc. No. Y13030) were deleted by PCR (Niehaus, F., Frey, B., Antranikian, A. (1997) *Gene,* 204, 153-158). Four mutations leading to amino acid exchanges were introduced during PCR. The amino acid exchanges (native→recombinant) are: L3F, A404T, S410C and L492H.

EXAMPLE 1

Site-Directed Mutagenesis and Expression of Tag DNA Polymerase Mutants

The cloning of the gene of Tag DNA Polymerase (polTY) was described earlier (Niehaus, F., Frey, B., Antranikian, A. (1997) *Gene,* 204, 153-158). Overexpression of Tag DNA Polymerase in *E. coli* was achieved by subcloning its encoding gene into the IPTG-inducible pET15b vector (Novagen) containing an N-terminal His-Tag for purification (the resulting plasmid was named pET15b-TagPol).

The mutants presented in this study were prepared in polymerase chain reactions using primers containing the desired mutations as a mismatch. The forward primer was universally "Kpn-fw", matching to a sequence about 100 bp upstream of the mutation site and contained a KpnI restriction site of the polTy gene. The reverse primers contained a SnaBI restriction site and additionally the desired mutation. The sequences of the oligonucleotides were as follows (mismatch sites for mutagenesis underlined):

```
Kpn-Fw
                                        SEQ. ID. NO: 1
5'-GCAACCTTGTAGAGTAGAGTGGTACCTGTTAAGGG-3';

TagY387F
                                        SEQ. ID. NO: 2
5'-GCCTCTTTCCGGCTCTTTTACGTATCCTCCCAGGAAAGTAGTCC-
3',

TagY387H
                                        SEQ. ID. NO:3
5'-GCCTCTTTGCGGCTCTTTTACGTATCCTCCCAGGTGAGTAGTCC-
3',

TagY387N
                                        SEQ. ID. NO: 4
5'-GCCTCTTTCCGGCTCTTTTACGTATCCTCCCAGGTTAGTAGTCC-
3',

TagY387S
                                        SEQ. ID. NO: 5
5'-GCCTCTTTCCGGCTCTTTTACGTATCCTCCCAGGGAAGTAGTCC-
3',

TagY387W
                                        SEQ. ID. NO: 6
5'-GCCTCTTTCCGGCTCTTTTACGTATCCTCCCAGCCAAGTAGTCC-
3',

TagG389A
                                        SEQ. ID. NO: 7
5'-GCCTCTTTCCGGCTCTTTTACGTATCCAGCCAGGTAAGTAGTCC-
3'.
```

PCR reactions were carried out with Expand™ High Fidelity PCR System (Roche Molecular Biochemicals) using the following program: 2 min 94° C., 30 cycles of 10 sec 94° C., 30 sec 55° C., 30 sec at 72° C. The resulting 139 bp fragments were digested with the restriction enzymes KpnI and SnaBI yielding a 101 bp fragment that was ligated into pET15b-TagPol linearized with the restriction enzymes KpnI and SnaBI. The cloned DNA fragments were sequenced to confirm the presence of the desired mutations.

For protein expression, *E. coli* BL21 (DE3) cells were transformed with the expression vector pET15b-TagPol.

Three to five colonies were inoculated in 15 ml of LB medium supplemented with 100 µg Ampicillin per ml and grown to $OD_{600nm}$ 0.3. An aliquot (10 ml) of the preculture was used to inoculate 500 ml of LB medium and incubated while shaking at 37° C. At $OD_{600nm}$=0.6 expression was induced by addition of IPTG (final concentration: 1 mM). After incubation for 3 hours cells were harvested by centrifugation and suspended in 50 mM Tris-HCl/pH 7.5, 10 mM KCl, 0.5 mM EDTA, 4 mM $MgCl_2$, 5 mM DTT. Cells were sonicated on ice and the crude extract was heated for 15 min to 80° C. Cell debris was removed by centrifugation (30 min, 30 000×g at 4° C.).

Figure 6:
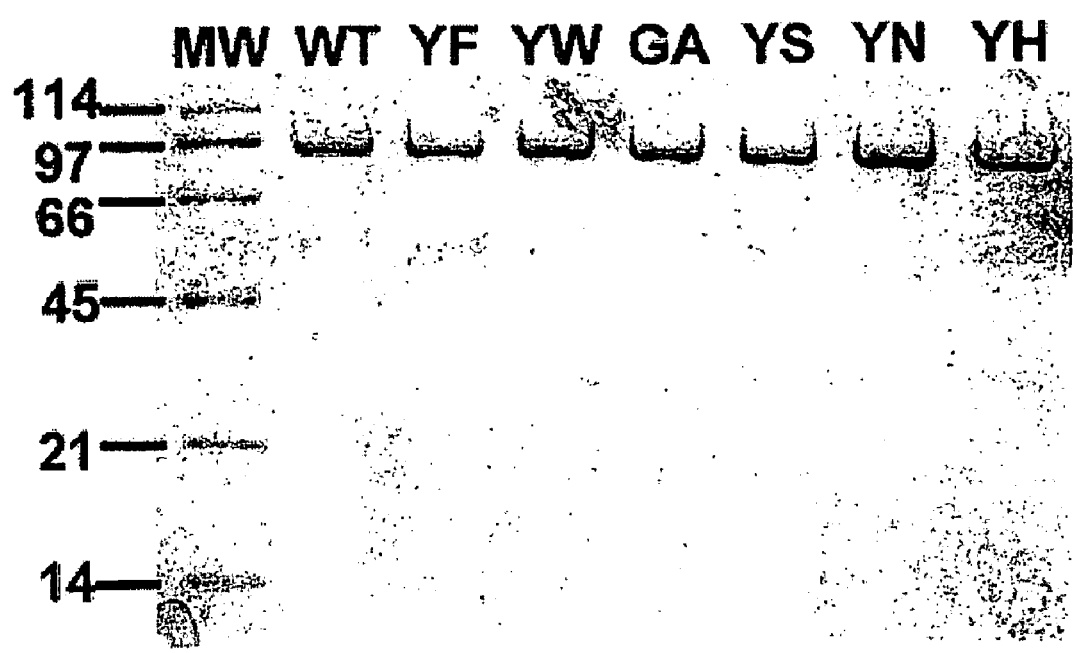
Figure 7:
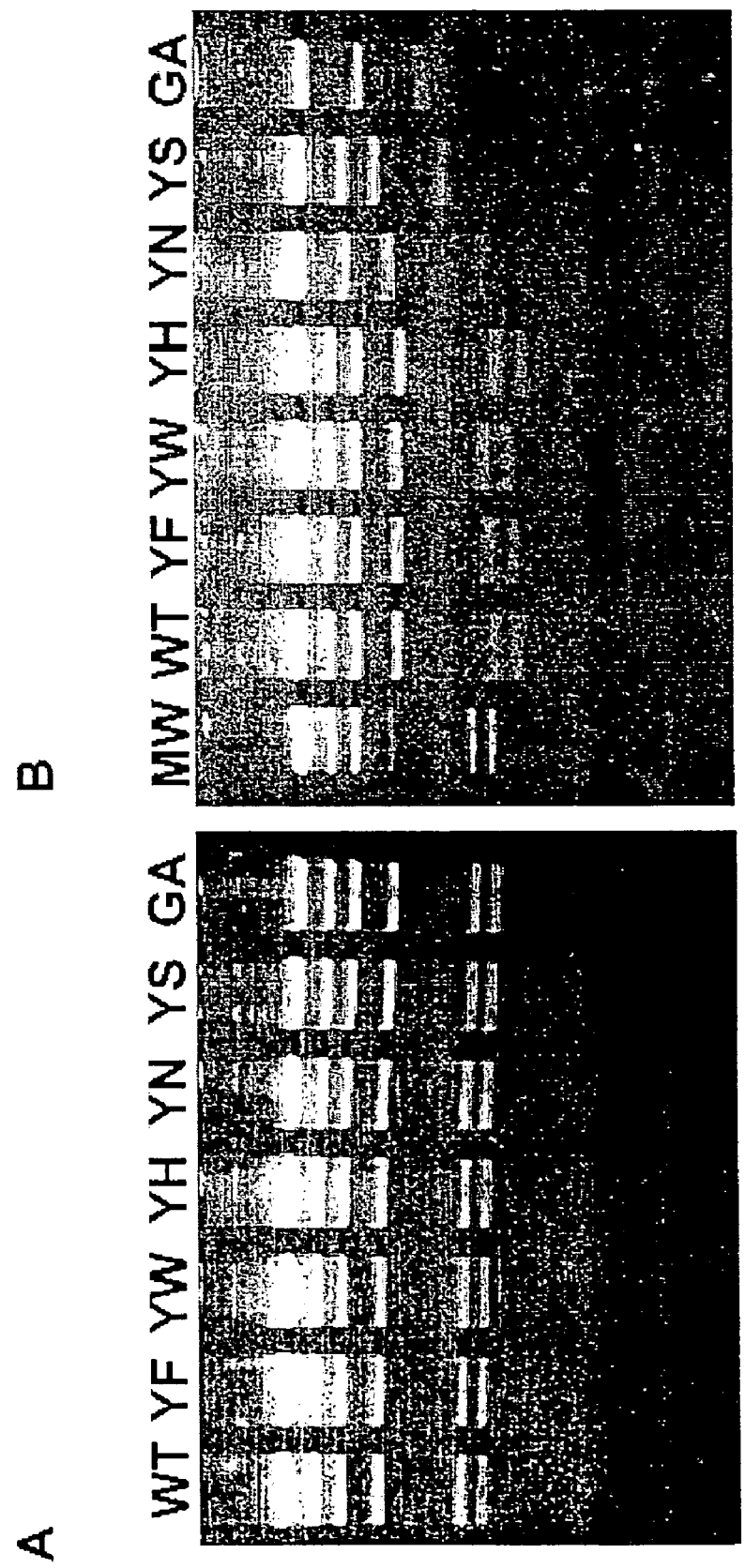

The supernatant was applied to a Blue Sepharose 3G-A column (Pharmacia) equilibrated with buffer A (50 mM Tris-HCl/pH 7.5, 10 mM KCl, 4 mM Mg $Cl_2$). The protein was eluted with a gradient of 0.01-1.5 M KCl. Active fractions were pooled and dialyzed against 20 mM Tris-HCl/pH 7.9, 5 mM imidazole, 500 mM NaCl. The sample was applied to a Ni-chelate column (Novagene) equilibrated in the same buffer and eluted with a gradient of 0.005-1 M imidazole. Active fractions were pooled and dialyzed against storage buffer (50 mM Tris-HCl/pH 7.5, 100 mM KCl, 0.5 mM EDTA, 5 mM DTT, 50% glycerol). The enzymes were pure as shown by SDS gel electrophoresis (FIG. 6).

EXAMPLE 2

DNA Polymerase Assay

The DNA polymerase activity was determined by measuring the incorporation of $\alpha$-($^{32}$P)dCTP in a DNA substrate. The test mix (50 µl) contained 5 µl 10× Tag reaction buffer (100 mM Tris-HCl/pH 8.9, 750 mM KCl, 15 MgCl2, 100 mM CHAPS), 200 µM of each dATP, dGTP, dTTP, 100 µM dCTP, 1 mCi $\alpha$-($^{32}$P)dCTP, 1 µg of M13 mp9 ssDNA annealed with 0.3 µg M13 primer. Assays were performed with 2 and 3 µl of enzyme in three different dilutions (final amount of enzyme 2.5 to 15 fmoles) yielding six reactions to calculate a mean value. As a reference Pwo DNA polymerase was used. The DNA/primer mix was prepared by heating 277.2 µg M13 mp9 ssDNA (Roche Molecular Biochemicals) and 156 µg M13 sequencing primer (17mer forward primer, Roche Molecular Biochemicals) for 30 minutes to 55° C. and then cooling it for 30 minutes to room temperature.

Assay reactions were incubated for 30 minutes at 65° C., stopped on ice by addition of 500 µl of 10% TCA (4° C.) and kept on ice for another 10 minutes. Samples were filtered over GFC-filter (Whatman), filters washed three times with 5% TCA, dried and submitted to β-counting in 2 ml of scintillation fluid. One unit is defined as the amount of enzyme necessary to incorporate 10 nM dNTP into acid insoluble material at 65° C. in 30 minutes.

EXAMPLE 3

Exonuclease Assays

Activity Assay

3 µl (300 ng) of enzyme (approximately 5 Units of polymerase activity) were incubated with 5 µg of 3H-labelled calf thymus DNA for 4 hours at 65° C. in a buffer containing 10 mM Tris-HCl/pH 8.9, 75 mM KCl, 1.5 $MgCl_2$, 10 mM CHAPS. Radioactivity liberated from calf thymus DNA was measured in a scintilation counter.

The assay used does not discriminate between the 3'-5' exonuclease activity and the 5'-3' exonuclease activity. 5'-3'-exonuclease activity has not been detected pheno- or genotypically in B-type polymerases of *Thermococcales* (Perler, F. B., Kumar, S. and Kong, H. (1996) *Adv. Prot Chem.*, 48, 377-435). Thus the values obtained can be regarded as 3'-5'-exonuclease activity.

In another assay, 1 µg of molecular weight marker II (Roche Molecular Biochemicals) were incubated in same buffer as above with 5 U of the indicated protein with or without 200 µM dNTP in a final volume of 50 µl for 6 hours at 65° C. The reaction products were separated by electrophoresis on 1% agarose gels.

3'-5' Exonuclease Processivity Assay

The previously described heparin trap method was used (Reddy, M. K., Weitzel, S. E. and von Hippel, P. H. (1992) *J. Biol. Chem.*, 267(20), 14157-14166; Pisani, F. M., De Felice, M. and Rossi, M. (1998) *Biochemistry*, 37(42), 15005-15012). A reaction mix (10 µl) containing 10 mM Tris-HCl/pH 8.9, 75 mM KCl, 10 mM CHAPS and 0.5 pmoles of a 5'-DIG-labeled 24mer oligonucleotide was prewarmed for 1 minute at 68° C. in a thermocycler. Unless otherwise noted, 1 pmol of the enzyme was preincubated for 1 minute at 68° C. with the substrate. The reaction was started by addition of $MnCl_2$ (final concentration: 4 mM) and heparin (final concentration: 1 mg/ml) to ensure single turnover conditions. After incubation for 4 minutes, the reaction was stopped by the addition of 5 µl of formamide buffer (80% formamide, 10 mM EDTA, 1 mg/ml bromophenol blue, 1 mg/ml xylene xyanol). The efficiency of the heparin trap was checked in a control reaction by adding heparin and $MnCl_2$ prior to the addition of the enzyme. The samples were denaturated for 3 minutes at 90° C. and subjected to denaturing gel electrophoresis on a 17.5% polyacrylamide/8 M urea gel. Gels were blotted to a positively charged nylon membrane (Roche Molecular Biochemicals) and the blots developed with CPD-Star (Roche Molecular Biochemicals) according to the manufacturers instructions.

EXAMPLE 4 lacI-Based PCR Fidelity Assay

We used the lacI-based PCR fidelity assay described by Frey and Suppmann (Frey, M. Suppmann, B. (1995) *Biochemica*, 2, 34-35). This method is based on the amplification, circularization and transformation of the pUC19 derivative pUCQ17, which contains a functional lacI$^q$ allele (Barnes, W. M. (1994) *Proc. Natl. Acad. Sci. USA*, 91, 2216-2220). PCR-derived mutations in lacI result in a de-repression of the expression of lacZα and subsequent formation of a functional β-galactosidase enzyme, which can be easily detected on X-Gal indicator plates.

The truncated lacI gene of pUC19 was substituted by a functional copy of lacI$^q$. A 178 bp *Pvu II-Afl III* fragment was replaced by a 1121 bp DNA fragment encoding lacI$^q$. The α-complementing *E. coli* strain DH5α, once transformed with the resulting plasmid pUCIQ17 (3632 bp), produces white (LACI$^+$) colonies on LB plates containing ampicillin (100 µg/ml) and X-Gal (0,004% w/v). For the PCR, pUCIQ17 was linearized by digestion with Dra II and used as a template in an amount of 1 or 10 ng. Both primers have Cla I cleavage sites at their 5' ends. Oligonucleotide Cla33 (34mer, 24 matches: SEQ. ID. NO: 8: 5'-AGC TTA TCG ATG GCA CTT TTC GGG GAA ATG TGC G-3') and Oligonucleotide Cla55 (36mer, 26 matches: SEQ. ID. NO: 9: 5'-AGC TTA TCG ATA AGC GGA TGC CGG GAG CAG ACA AGC-3') resulted in a PCR product of 3493 bp. The reactions were performed with 1 or 5 pmol of protein in the Tag polymerase PCR buffer described below or for the control reactions in the manufacturers PCR buffers with 2.5 U of enzyme. The cycle conditions were 10 sec denaturation at 94° C., 30 sec annealing at 57° C. and 4 min elongation at 72° C. for 18, 24 or 30 cycles depending on the enzyme.

After PCR, the yield of amplification product was determined at ($OD_{260nm}$ or in agarose gel) and the DNA fragments submitted to phenol/chloroform extraction to eliminate any protein. After digestion with ClaI, the DNA fragments were purified from a preparative agarose gel. Ligation reactions were carried out with the Rapid Ligation Kit (Roche Molecular Biochemicals), the reactions contained 30 ng DNA. The resulting circular plasmids were transformed in *E. coli* DH5α as described by Hanahan (Hanahan, D. (1983) *J. Mol. Biol.*, 166, 557-580) and plated on LB Amp/X-Gal plates described above. After incubation overnight at 37° C., blue and white colonies were counted. The error rate (f) per bp was calculated with a rearranged equation published by Keohavong and Thilly (Keohavong, P. and Thilly, W. G. (1989) *Proc Natl. Acad. Sci. USA*, 86, 9253-9257): f=–lnF/d×b bp.

Where F is the fraction of white colonies (white colonies/total colonies); d is the number of DNA duplications: $2^d$=output DNA/input DNA and b is the effective target size (1080 bp) of the lacI gene. There are 349 phenotypically identified (by colour screening) single-base substitutions (non-sense and mis-sense) at 179 codons (approximately 50% of the coding region) within the lacI gene. (Provost, G. S., Kretz, P. L., Hamner, R. T., Matthews, C. D., Rogers, B. J., Lundberg, K. S., Dycaico, M. J. and Short, J. M. (1993) *Mut. research*, 288, 133-149). Frameshift errors which may occur at every position in the 1080 bp open reading frame of lacI, are not taken into account because little information is available for the specific polymerases used in PCR systems except for Taq DNA polymerase.

EXAMPLE 5

Polymerase Chain Reactions

PCR was performed in a buffer optimized for Tag DNA polymerase and its mutants: 10 mM Tris-HCl/pH 8.9, 75 mM KCl, 1.5 $MgCl_2$, 10 mM CHAPS, 200 µM dNTP. 10 ng of λ DNA were used as a template and 30 pmol of each primer (20 bp, designed to yield the products of the desired length):

```
Lambda 1, universal forward primer:
                                      SEQ. ID. NO: 10
5'-GAT GAG TTC GTG TCC GTA CAA CA-3', SEQ. ID. NO: 11
Lambda 3.3: 5'-CTC ATC AGC AGA TCA TCT TCA GG-3', SEQ. ID. NO: 12
Lambda 8: 5'-ACT CCA GCG TCT CAT CTT TAT GC-3', SEQ. ID. NO: 13
Lambda 9: 5'-GAT GGT GAT CCT CTC TCG TTT GC-3'.
```

Lambda 3.3, 8 and 9 were used as reverse primers for the amplification of 3.3 kb, 5 kb and 7.5 kb fragments respectively.

Template, primers and nucleotides were prepared in mix 1 in a volume of 25 µl. Then 25 µl of mix 2 containing the buffer and enzyme (1 pmol Tag wild type or mutant; or 2.5 U control enzyme) were added. All reactions were prepared in duplicate. The amplification was performed in a 2400 GeneAmp thermocycler (Perkin Elmer). The cycle conditions were: 2 min at 94° C., 10 cycles with 10 sec denaturation at 94° C., 30 sec annealing at 58° C. and elongation at 72° C.

Elongation times depended on the length of the product (3 min for 3.3 kb, 4.3 min for 5 kb and 7 min for 7,5 kb). Another 20 cycles were performed with increasing the elongation times by 20 sec/cycle. The reaction was finished by 7 minutes at 72° C. The tubes were kept at 4° C. until separation by electrophoresis on 1% agarose gels.

The improvement of the PCR performance of the mutants was also studied in a "time-dependent PCR". A 2 kb fragment was amplified from lambda DNA as described above. In these studies the elongation time of the PCR was stepwise reduced (90 sec, 40 sec, 30 sec) to determine for each enzyme the minimal elongation time that was sufficient to amplify the 2 kb fragment. The following primers were used:

```
Lambda 1, universal forward primer:
                                      SEQ. ID. NO: 14
5'-GAT GAG TTC GTG TCC GTA CAA CA-3', Lambda 6, reverse primer:
                                      SEQ. ID. NO: 15
5'-CTT CAT CAT CGA GAT AGC TGT CG-3',
```

The temperature profile was as described above. The elongation times were kept constant over 30 cycles.

---

What is claimed is:

1. A thermostable mutant polymerase comprising a Y-GG/A amino acid motif between an N-terminal 3'-5' exonuclease domain and a C-terminal polymerase domain wherein the tyrosine of the Y-GG/A amino acid motif is substituted with another amino acid, wherein the mutant polymerase is suitable for polymerase chain reactions, and wherein the mutant polymerase has at least 80% amino acid homology to SEQ ID NO:34.

2. The mutant polymerase of claim 1, wherein the difference between the mutant polymerase and wild type polymerase consists of the single amino acid substitution of the tyrosine of the Y-GG/A amino acid motif, wherein the wild type polymerase is a polymerase isolated from a bacterium selected from the group consisting of *Thermococcus aggregans, Thermococcus litoralis, Thermococcus gorgonarius, Thermococcus furiosus, Thermococcus* spec. 9N7, *Pyrococcus abysii, Pyrococcus horikoshii, Pyrococcus* spec. KOD, and *Pyrococcus furiosus*.

3. The mutant polymerase of claim 1, wherein the wild-type form of the mutant polymerase is obtainable from Euryarchaea.

4. The mutant polymerase of claim 1, wherein the wild-type form of the mutant polymerase is obtainable from *Thermococcus aggregans*.

5. The mutant polymerase of claim 1, wherein the tyrosine of the Y-GG/A amino acid motif is substituted with an amino acid with an aromatic side chain.

6. The mutant polymerase of claim 5, wherein the tyrosine of the Y-GG/A amino acid motif is substituted with a phenylalanine, a tryptophan or a histidine.

7. The mutant polymerase of claim 1, wherein the tyrosine of the Y-GG/A amino acid motif is substituted with an amino acid with a hydrophilic side chain.

8. The mutant polymerase of claim 7, wherein the tyrosine of the Y-GG/A amino acid motif is substituted with an asparagine.

9. The mutant polymerase of claim 6, wherein the tyrosine of the Y-GG/A amino acid motif is substituted with a tryptophan or a histidine.

10. The mutant polymerase of claim 7, wherein the tyrosine of the Y-GG/A amino acid motif is substituted with a serine.

11. A DNA encoding the mutant polymerase of claim 1.

12. A vector comprising the DNA of claim 11.

13. An isolated host cell comprising the DNA of claim 11 or the vector of claim 12.

14. A process for obtaining a mutant polymerase comprising purifying the mutant polymerase from the isolated host cell of claim 13.

15. A process for synthesizing nucleic acids, comprising contacting the mutant polymerase of claim 1 with nucleotides, a primer and a polynucleotide template under conditions suitable for elongation of the primer.

16. A process for polynucleotide amplification comprising contacting the mutant polymerase of claim 1 with nucleotides, primers and a polynucleotide template under conditions suitable for amplification of the polynucleotide.

17. A polymerase chain reaction process comprising contacting the mutant polymerase of claim 1 with nucleotides, a primer and a polynucleotide template under conditions suitable for amplification of the polynucleotide template.

18. The mutant polymerase of claim 1, wherein the Y-GG/A amino acid motif between the N-terminal 3'-5' exonuclease domain and the C-terminal polymerase domain comprises E--RR-R--Y-GG(Y/F)VKE(P/R)E-GLWEN (SEQ ID NO:36).

19. The mutant polymerase of claim 1, wherein the mutant polymerase has at least 85% amino acid homology to SEQ ID NO:34.

* * * * *

SEQUENCE LISTING

<160> NUMBER OF SEQ ID NOS: 34

<210> SEQ ID NO 1
<211> LENGTH: 35
<212> TYPE: DNA
<213> ORGANISM: Artificial
<220> FEATURE:
<223> OTHER INFORMATION: amplification primer

<400> SEQUENCE: 1
gcaaccttgt agagtagagt ggtacctgtt aaggg                    35

<210> SEQ ID NO 2
<211> LENGTH: 44
<212> TYPE: DNA

```
<213> ORGANISM: Artificial
<220> FEATURE:
<223> OTHER INFORMATION: amplification primer

<400> SEQUENCE: 2 gcctcttttcc ggctctttta cgtatcctcc caggaaagta gtcc                    44

<210> SEQ ID NO 3
<211> LENGTH: 44
<212> TYPE: DNA
<213> ORGANISM: Artificial
<220> FEATURE:
<223> OTHER INFORMATION: amplification primer

<400> SEQUENCE: 3 gcctcttttcc ggctctttta cgtatcctcc caggtgagta gtcc                    44

<210> SEQ ID NO 4
<211> LENGTH: 44
<212> TYPE: DNA
<213> ORGANISM: Artificial
<220> FEATURE:
<223> OTHER INFORMATION: amplification primer

<400> SEQUENCE: 4 gcctcttttcc ggctctttta cgtatcctcc caggttagta gtcc                    44

<210> SEQ ID NO 5
<211> LENGTH: 44
<212> TYPE: DNA
<213> ORGANISM: Artificial
<220> FEATURE:
<223> OTHER INFORMATION: amplification primer

<400> SEQUENCE: 5 gcctcttttcc ggctctttta cgtatcctcc cagggaagta gtcc                    44

<210> SEQ ID NO 6
<211> LENGTH: 44
<212> TYPE: DNA
<213> ORGANISM: Artificial
<220> FEATURE:
<223> OTHER INFORMATION: amplification primer

<400> SEQUENCE: 6 gcctcttttcc ggctctttta cgtatcctcc cagccaagta gtcc                    44

<210> SEQ ID NO 7
<211> LENGTH: 44
<212> TYPE: DNA
<213> ORGANISM: Artificial
<220> FEATURE:
<223> OTHER INFORMATION: amplification primer

<400> SEQUENCE: 7 gcctcttttcc ggctctttta cgtatccagc caggtaagta gtcc                    44

<210> SEQ ID NO 8
<211> LENGTH: 34
<212> TYPE: DNA
<213> ORGANISM: Artificial
<220> FEATURE:
<223> OTHER INFORMATION: amplification primer

<400> SEQUENCE: 8
agcttatcga tggcactttt cggggaaatg tgcg                                34
```

```
<210> SEQ ID NO 9
<211> LENGTH: 36
<212> TYPE: DNA
<213> ORGANISM: Artificial
<220> FEATURE:
<223> OTHER INFORMATION: amplification primer

<400> SEQUENCE: 9
agcttatcga taagcggatg ccgggagcag acaagc                              36

<210> SEQ ID NO 10
<211> LENGTH: 23
<212> TYPE: DNA
<213> ORGANISM: Artificial
<220> FEATURE:
<223> OTHER INFORMATION: amplification primer

<400> SEQUENCE: 10
gatgagttcg tgtccgtaca aca                                            23

<210> SEQ ID NO 11
<211> LENGTH: 23
<212> TYPE: DNA
<213> ORGANISM: Artificial
<220> FEATURE:
<223> OTHER INFORMATION: amplification primer

<400> SEQUENCE: 11
ctcatcagca gatcatcttc agg                                            23

<210> SEQ ID NO 12
<211> LENGTH: 23
<212> TYPE: DNA
<213> ORGANISM: Artificial
<220> FEATURE:
<223> OTHER INFORMATION: amplification primer

<400> SEQUENCE: 12
actccagcgt ctcatcttta tgc                                            23

<210> SEQ ID NO 13
<211> LENGTH: 23
<212> TYPE: DNA
<213> ORGANISM: Artificial
<220> FEATURE:
<223> OTHER INFORMATION: amplification primer

<400> SEQUENCE: 13
gatggtgatc ctctctcgtt tgc                                            23

<210> SEQ ID NO 14
<211> LENGTH: 23
<212> TYPE: DNA
<213> ORGANISM: Artificial
<220> FEATURE:
<223> OTHER INFORMATION: amplification primer

<400> SEQUENCE: 14
gatgagttcg tgtccgtaca aca                                            23

<210> SEQ ID NO 15
<211> LENGTH: 23
<212> TYPE: DNA
<213> ORGANISM: Artificial
<220> FEATURE:
```

```
<223> OTHER INFORMATION: amplification primer

<400> SEQUENCE: 15
cttcatcatc gagatagctg tcg                                             23

<210> SEQ ID NO 16
<211> LENGTH: 25
<212> TYPE: PRT
<213> ORGANISM: T. aggregans

<400> SEQUENCE: 16

Glu Tyr Arg Arg Arg Leu Arg Thr Thr Tyr Leu Gly Gly Tyr Val Lys
1               5                   10                  15

Glu Pro Glu Arg Gly Leu Trp Glu Asn
            20                  25

<210> SEQ ID NO 17
<211> LENGTH: 25
<212> TYPE: PRT
<213> ORGANISM: T. litoralis

<400> SEQUENCE: 17

Glu Tyr Lys Arg Arg Leu Arg Thr Thr Tyr Leu Gly Gly Tyr Val Lys
1               5                   10                  15

Glu Pro Glu Lys Gly Leu Trp Glu Asn
            20                  25

<210> SEQ ID NO 18
<211> LENGTH: 24
<212> TYPE: PRT
<213> ORGANISM: T. fumicolans

<400> SEQUENCE: 18

Glu Leu Glu Arg Arg Arg Gly Gly Tyr Ala Gly Gly Tyr Val Lys Glu
1               5                   10                  15

Pro Glu Arg Gly Leu Trp Glu Asn
            20

<210> SEQ ID NO 19
<211> LENGTH: 24
<212> TYPE: PRT
<213> ORGANISM: T. spec. 9N7

<400> SEQUENCE: 19

Glu Leu Ala Arg Arg Arg Gly Gly Tyr Ala Gly Gly Tyr Val Lys Glu
1               5                   10                  15

Arg Glu Arg Gly Leu Trp Glu Asn
            20

<210> SEQ ID NO 20
<211> LENGTH: 24
<212> TYPE: PRT
<213> ORGANISM: T. gorgonarius

<400> SEQUENCE: 20

Glu Leu Ala Arg Arg Arg Glu Ser Tyr Ala Gly Gly Tyr Val Lys Glu
1               5                   10                  15

Pro Glu Arg Gly Leu Trp Glu Asn
            20

<210> SEQ ID NO 21
<211> LENGTH: 24
```

```
<212> TYPE: PRT
<213> ORGANISM: P. spec. KOD

<400> SEQUENCE: 21

Glu Leu Ala Arg Arg Gln Ser Tyr Glu Gly Gly Tyr Val Lys Glu
1               5                   10                  15

Pro Glu Arg Gly Leu Trp Glu Asn
            20

<210> SEQ ID NO 22
<211> LENGTH: 25
<212> TYPE: PRT
<213> ORGANISM: P. abysii

<400> SEQUENCE: 22

Glu Tyr Glu Arg Arg Leu Arg Glu Ser Tyr Gly Gly Tyr Val Lys
1               5                   10                  15

Glu Pro Glu Lys Gly Leu Trp Glu Asn
            20                  25

<210> SEQ ID NO 23
<211> LENGTH: 25
<212> TYPE: PRT
<213> ORGANISM: P. furiosus

<400> SEQUENCE: 23

Glu Tyr Gln Arg Arg Leu Arg Glu Ser Tyr Thr Gly Gly Phe Val Lys
1               5                   10                  15

Glu Pro Glu Lys Gly Leu Trp Glu Asn
            20                  25

<210> SEQ ID NO 24
<211> LENGTH: 25
<212> TYPE: PRT
<213> ORGANISM: P. horikoshii

<400> SEQUENCE: 24

Glu Tyr Glu Arg Arg Leu Arg Glu Ser Tyr Glu Gly Gly Tyr Val Lys
1               5                   10                  15

Glu Pro Glu Lys Gly Leu Trp Glu Asn
            20                  25

<210> SEQ ID NO 25
<211> LENGTH: 25
<212> TYPE: PRT
<213> ORGANISM: M. jannaschii

<400> SEQUENCE: 25

Glu Tyr Arg Arg Arg Val Leu Thr Thr Tyr Gly Gly Tyr Val Lys
1               5                   10                  15

Glu Pro Glu Lys Gly Met Phe Glu Asp
            20                  25

<210> SEQ ID NO 26
<211> LENGTH: 25
<212> TYPE: PRT
<213> ORGANISM: M. voltae

<400> SEQUENCE: 26

Ser Tyr Arg Glu Arg Ala Lys Phe Ser Tyr Glu Gly Gly Tyr Val Arg
1               5                   10                  15

Glu Pro Leu Lys Gly Ile Gln Glu Asn
```

-continued

```
                20                  25

<210> SEQ ID NO 27
<211> LENGTH: 25
<212> TYPE: PRT
<213> ORGANISM: S. solfataricus

<400> SEQUENCE: 27

Thr Ser Ala Leu Ile Lys Gly Lys Gly Tyr Lys Gly Ala Val Val Ile
1               5                   10                  15

Asp Pro Pro Ala Gly Ile Phe Phe Asn
            20                  25

<210> SEQ ID NO 28
<211> LENGTH: 25
<212> TYPE: PRT
<213> ORGANISM: S. acidocaldarius

<400> SEQUENCE: 28

Thr Ala Ala Val Ile Lys Gly Lys Lys Tyr Lys Gly Ala Val Val Ile
1               5                   10                  15

Asp Pro Pro Ala Gly Val Tyr Phe Asn
            20                  25

<210> SEQ ID NO 29
<211> LENGTH: 25
<212> TYPE: PRT
<213> ORGANISM: P. islandicum

<400> SEQUENCE: 29

Thr Lys Ala Ile Ile Lys Gly Lys Lys Tyr Ala Gly Ala Val Val Leu
1               5                   10                  15

Asp Pro Pro Leu Gly Ile Phe Phe Asn
            20                  25

<210> SEQ ID NO 30
<211> LENGTH: 25
<212> TYPE: PRT
<213> ORGANISM: P. occultum

<400> SEQUENCE: 30

Ser Glu Ala Leu Ile Lys Gly Lys Lys Tyr Gln Gly Ala Leu Val Leu
1               5                   10                  15

Asp Pro Pro Ser Gly Ile Tyr Phe Asn
            20                  25

<210> SEQ ID NO 31
<211> LENGTH: 25
<212> TYPE: PRT
<213> ORGANISM: A. pernix

<400> SEQUENCE: 31

Val Gly Ala Ile Ile Lys Asp Lys Lys Tyr Arg Gly Ala Ile Val Leu
1               5                   10                  15

Asp Pro Pro Val Gly Ile Phe Phe Arg
            20                  25

<210> SEQ ID NO 32
<211> LENGTH: 25
<212> TYPE: PRT
<213> ORGANISM: S. chwakuensis

<400> SEQUENCE: 32
```

-continued

```
Thr Ala Ala Ile Ser Lys Gly Lys Arg Tyr Lys Gly Ala Val Val Ile
1               5                   10                  15

Asp Pro Pro Ala Gly Val Phe Phe Asn
            20                  25

<210> SEQ ID NO 33
<211> LENGTH: 2325
<212> TYPE: DNA
<213> ORGANISM: T. aggregans
<220> FEATURE:
<221> NAME/KEY: CDS
<222> LOCATION: (1)..(2325)

<400> SEQUENCE: 33
```

| | | | | | | | | | | | | | | | | |
|---|---|---|---|---|---|---|---|---|---|---|---|---|---|---|---|---|
| atg | ata | ttt | gac | act | gac | tac | ata | aca | aag | gac | ggt | aaa | ccc | ata | att | 48 |
| Met | Ile | Phe | Asp | Thr | Asp | Tyr | Ile | Thr | Lys | Asp | Gly | Lys | Pro | Ile | Ile | |
| 1 | | | | 5 | | | | | 10 | | | | | 15 | | |
| cga | att | ttc | aag | aaa | gag | aac | ggg | gaa | ttt | aaa | ata | gaa | ctt | gat | cca | 96 |
| Arg | Ile | Phe | Lys | Lys | Glu | Asn | Gly | Glu | Phe | Lys | Ile | Glu | Leu | Asp | Pro | |
| | | | 20 | | | | | 25 | | | | | 30 | | | |
| cat | ttt | cag | ccc | tac | att | tac | gct | ctt | ctc | aaa | gat | gac | tcc | gct | att | 144 |
| His | Phe | Gln | Pro | Tyr | Ile | Tyr | Ala | Leu | Leu | Lys | Asp | Asp | Ser | Ala | Ile | |
| | | 35 | | | | | 40 | | | | | 45 | | | | |
| gat | gaa | ata | aaa | gca | ata | aaa | ggc | gag | aga | cac | gga | aaa | att | gtg | aga | 192 |
| Asp | Glu | Ile | Lys | Ala | Ile | Lys | Gly | Glu | Arg | His | Gly | Lys | Ile | Val | Arg | |
| | 50 | | | | | 55 | | | | | 60 | | | | | |
| gta | gtc | gat | gca | gtg | aaa | gtc | aag | aag | aaa | ttt | ttg | ggg | aga | gat | gtt | 240 |
| Val | Val | Asp | Ala | Val | Lys | Val | Lys | Lys | Lys | Phe | Leu | Gly | Arg | Asp | Val | |
| 65 | | | | 70 | | | | | 75 | | | | | 80 | | |
| gag | gtc | tgg | aag | ctt | ata | ttt | gag | cat | ccc | caa | gac | gtc | ccg | gcc | cta | 288 |
| Glu | Val | Trp | Lys | Leu | Ile | Phe | Glu | His | Pro | Gln | Asp | Val | Pro | Ala | Leu | |
| | | | 85 | | | | | 90 | | | | | 95 | | | |
| agg | ggc | aag | ata | agg | gaa | cat | cca | gct | gtg | att | gac | att | tat | gag | tac | 336 |
| Arg | Gly | Lys | Ile | Arg | Glu | His | Pro | Ala | Val | Ile | Asp | Ile | Tyr | Glu | Tyr | |
| | | 100 | | | | | 105 | | | | | 110 | | | | |
| gac | ata | ccc | ttt | gcc | aag | cgc | tac | ctc | ata | gac | aag | ggc | ttg | atc | cct | 384 |
| Asp | Ile | Pro | Phe | Ala | Lys | Arg | Tyr | Leu | Ile | Asp | Lys | Gly | Leu | Ile | Pro | |
| | 115 | | | | | 120 | | | | | 125 | | | | | |
| atg | gag | ggc | gac | gag | gag | ctt | aag | cta | atg | gcc | ttc | gac | att | gag | acg | 432 |
| Met | Glu | Gly | Asp | Glu | Glu | Leu | Lys | Leu | Met | Ala | Phe | Asp | Ile | Glu | Thr | |
| 130 | | | | 135 | | | | | 140 | | | | | | | |
| ttt | tac | cac | gag | gga | gac | gag | ttt | ggg | aag | ggc | gag | ata | ata | atg | ata | 480 |
| Phe | Tyr | His | Glu | Gly | Asp | Glu | Phe | Gly | Lys | Gly | Glu | Ile | Ile | Met | Ile | |
| 145 | | | | 150 | | | | | 155 | | | | | 160 | | |
| agc | tac | gcc | gat | gag | gaa | gag | gca | agg | gta | att | aca | tgg | aag | aat | att | 528 |
| Ser | Tyr | Ala | Asp | Glu | Glu | Glu | Ala | Arg | Val | Ile | Thr | Trp | Lys | Asn | Ile | |
| | | | | 165 | | | | | 170 | | | | | 175 | | |
| gat | ctg | ccc | tac | gtt | gat | gtt | gta | tcc | aac | gaa | agg | gag | atg | ata | aag | 576 |
| Asp | Leu | Pro | Tyr | Val | Asp | Val | Val | Ser | Asn | Glu | Arg | Glu | Met | Ile | Lys | |
| | | | 180 | | | | | 185 | | | | | 190 | | | |
| cgg | ttt | gtg | caa | att | gtc | agg | gaa | aaa | gac | ccg | gat | gtc | ctg | ata | act | 624 |
| Arg | Phe | Val | Gln | Ile | Val | Arg | Glu | Lys | Asp | Pro | Asp | Val | Leu | Ile | Thr | |
| | | 195 | | | | | 200 | | | | | 205 | | | | |
| tac | aat | gga | gac | aac | ttt | gat | ttg | ccg | tac | ctt | ata | aaa | agg | gca | gag | 672 |
| Tyr | Asn | Gly | Asp | Asn | Phe | Asp | Leu | Pro | Tyr | Leu | Ile | Lys | Arg | Ala | Glu | |
| | 210 | | | | | 215 | | | | | 220 | | | | | |
| aag | tta | gga | gtt | act | ctt | ctc | ttg | ggg | agg | gac | aaa | gaa | cac | ccc | gag | 720 |
| Lys | Leu | Gly | Val | Thr | Leu | Leu | Leu | Gly | Arg | Asp | Lys | Glu | His | Pro | Glu | |
| 225 | | | | 230 | | | | | 235 | | | | | 240 | | |
| ccc | aag | att | cac | aga | atg | ggc | gat | agc | ttt | gcc | gtg | gaa | att | aaa | ggc | 768 |

```
              Pro Lys Ile His Arg Met Gly Asp Ser Phe Ala Val Glu Ile Lys Gly
                      245                 250                 255 aga att cac ttt gat ctc ttc ccg gtt gtg cgg aga acc ata aac ctc        816
Arg Ile His Phe Asp Leu Phe Pro Val Val Arg Arg Thr Ile Asn Leu
            260                 265                 270 cca aca tac acg ctt gag gca gtt tat gaa gcc gtc ttg gga aaa acc        864
Pro Thr Tyr Thr Leu Glu Ala Val Tyr Glu Ala Val Leu Gly Lys Thr
            275                 280                 285 aaa agc aag ctg ggt gcg gag gaa atc gcc gcc atc tgg gaa aca gag        912
Lys Ser Lys Leu Gly Ala Glu Glu Ile Ala Ala Ile Trp Glu Thr Glu
        290                 295                 300 gag agc atg aag aag ctg gcc cag tac tcg atg gaa gat gct agg gca        960
Glu Ser Met Lys Lys Leu Ala Gln Tyr Ser Met Glu Asp Ala Arg Ala
305                 310                 315                 320 act tat gaa ctc gga aaa gag ttt ttc ccc atg gag gca gag cta gca       1008
Thr Tyr Glu Leu Gly Lys Glu Phe Phe Pro Met Glu Ala Glu Leu Ala
                325                 330                 335 aag cta ata ggc caa agc gta tgg gac gtc tca aga tca agc act ggc       1056
Lys Leu Ile Gly Gln Ser Val Trp Asp Val Ser Arg Ser Ser Thr Gly
                340                 345                 350 aac ctt gta gag tgg tac ctg tta agg gtg gca tat gag agg aat gag       1104
Asn Leu Val Glu Trp Tyr Leu Leu Arg Val Ala Tyr Glu Arg Asn Glu
            355                 360                 365 ctc gct ccg aac aag ccg gat gaa gaa gag tac aga agg cgt tta agg       1152
Leu Ala Pro Asn Lys Pro Asp Glu Glu Glu Tyr Arg Arg Arg Leu Arg
        370                 375                 380 act act tac ctg gga gga tac gta aaa gag ccg gaa aga ggc tta tgg       1200
Thr Thr Tyr Leu Gly Gly Tyr Val Lys Glu Pro Glu Arg Gly Leu Trp
385                 390                 395                 400 gag aac atc acc tat tta gac ttt agg tgc cta tac ccc tca att ata       1248
Glu Asn Ile Thr Tyr Leu Asp Phe Arg Cys Leu Tyr Pro Ser Ile Ile
                405                 410                 415 gtt acc cac aac gtc tcc cct gac act tta gaa aga gaa ggc tgc aag       1296
Val Thr His Asn Val Ser Pro Asp Thr Leu Glu Arg Glu Gly Cys Lys
                420                 425                 430 aat tac gat gtt gcc ccg ata gta ggt tat aag ttc tgc aag gat ttt       1344
Asn Tyr Asp Val Ala Pro Ile Val Gly Tyr Lys Phe Cys Lys Asp Phe
            435                 440                 445 ccc ggt ttc att cca tct ata ctc ggg gaa tta atc aca atg agg caa       1392
Pro Gly Phe Ile Pro Ser Ile Leu Gly Glu Leu Ile Thr Met Arg Gln
        450                 455                 460 gaa ata aag aag aag atg aaa gct aca att gac cca ata gaa aag aaa       1440
Glu Ile Lys Lys Lys Met Lys Ala Thr Ile Asp Pro Ile Glu Lys Lys
465                 470                 475                 480 atg ctt gat tat agg caa aga gct gtt aaa ttg cac gca aac agc tat       1488
Met Leu Asp Tyr Arg Gln Arg Ala Val Lys Leu His Ala Asn Ser Tyr
                485                 490                 495 tac ggt tat atg ggc tat ccc aag gcg agg tgg tac tcg aag gaa tgt       1536
Tyr Gly Tyr Met Gly Tyr Pro Lys Ala Arg Trp Tyr Ser Lys Glu Cys
                500                 505                 510 gcc gaa agc gtt acc gcg tgg gga agg cac tac ata gaa atg acc ata       1584
Ala Glu Ser Val Thr Ala Trp Gly Arg His Tyr Ile Glu Met Thr Ile
            515                 520                 525 aaa gag ata gag gag aaa ttt gga ttt aag gtg cta tat gcc gac act       1632
Lys Glu Ile Glu Glu Lys Phe Gly Phe Lys Val Leu Tyr Ala Asp Thr
        530                 535                 540 gat ggt ttt tac gcc aca ata ccg gga gaa aaa cct gaa aca atc aaa       1680
Asp Gly Phe Tyr Ala Thr Ile Pro Gly Glu Lys Pro Glu Thr Ile Lys
545                 550                 555                 560
```

-continued

```
aag aaa gct aag gaa ttc tta aaa tac ata aac tcc aaa ctt ccc ggt    1728
Lys Lys Ala Lys Glu Phe Leu Lys Tyr Ile Asn Ser Lys Leu Pro Gly
            565                 570                 575 ctg ctc gag ctt gag tat gag ggc ttt tac ttg aga gga ttt ttc gtc    1776
Leu Leu Glu Leu Glu Tyr Glu Gly Phe Tyr Leu Arg Gly Phe Phe Val
        580                 585                 590 gca aag aag cgc tat gcg gtt ata gac gaa gaa ggt agg ata acg aca    1824
Ala Lys Lys Arg Tyr Ala Val Ile Asp Glu Glu Gly Arg Ile Thr Thr
    595                 600                 605 agg ggt ctg gaa gtt gta agg agg gac tgg agc gaa ata gcc aaa gag    1872
Arg Gly Leu Glu Val Val Arg Arg Asp Trp Ser Glu Ile Ala Lys Glu
610                 615                 620 acc cag gct aaa gtc ttg gag gca ata ctt aaa gaa gat agt gtc gaa    1920
Thr Gln Ala Lys Val Leu Glu Ala Ile Leu Lys Glu Asp Ser Val Glu
625                 630                 635                 640 aaa gct gtg gaa atc gtt aag gac gtt gtt gag gag ata gca aaa tac    1968
Lys Ala Val Glu Ile Val Lys Asp Val Val Glu Glu Ile Ala Lys Tyr
            645                 650                 655 caa gtc ccg ctt gaa aag ctt gtt atc cac gag cag att acc aag gat    2016
Gln Val Pro Leu Glu Lys Leu Val Ile His Glu Gln Ile Thr Lys Asp
        660                 665                 670 cta agt gaa tac aaa gcc att ggg cct cat gta gca ata gca aag agg    2064
Leu Ser Glu Tyr Lys Ala Ile Gly Pro His Val Ala Ile Ala Lys Arg
    675                 680                 685 ctt gct gca aag gga ata aaa gtg aga ccc ggc acg ata ata agc tat    2112
Leu Ala Ala Lys Gly Ile Lys Val Arg Pro Gly Thr Ile Ile Ser Tyr
690                 695                 700 atc gtc ctc agg gga agc gga aag ata agt gac agg gta att ttg ctt    2160
Ile Val Leu Arg Gly Ser Gly Lys Ile Ser Asp Arg Val Ile Leu Leu
705                 710                 715                 720 tca gag tat gat ccg aaa aaa cac aag tac gac ccc gac tac tac ata    2208
Ser Glu Tyr Asp Pro Lys Lys His Lys Tyr Asp Pro Asp Tyr Tyr Ile
            725                 730                 735 gaa aac caa gtt ctg ccg gcg gtg ctt agg atc ctt gaa gcc ttc ggc    2256
Glu Asn Gln Val Leu Pro Ala Val Leu Arg Ile Leu Glu Ala Phe Gly
        740                 745                 750 tac aga aaa gag gac tta aaa tac caa agc tca aaa cag gtt gga ctg    2304
Tyr Arg Lys Glu Asp Leu Lys Tyr Gln Ser Ser Lys Gln Val Gly Leu
    755                 760                 765 gac gcg tgg ctt aag aag tag                                        2325
Asp Ala Trp Leu Lys Lys
    770
```

<210> SEQ ID NO 34
<211> LENGTH: 774
<212> TYPE: PRT
<213> ORGANISM: T. aggregans

<400> SEQUENCE: 34

```
Met Ile Phe Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Asp Glu Ile Lys Ala Ile Lys Gly Glu Arg His Gly Lys Ile Val Arg
    50                  55                  60

Val Val Asp Ala Val Lys Val Lys Lys Lys Phe Leu Gly Arg Asp Val
65                  70                  75                  80
```

-continued

```
Glu Val Trp Lys Leu Ile Phe Glu His Pro Gln Asp Val Pro Ala Leu
            85                  90                  95

Arg Gly Lys Ile Arg Glu His Pro Ala Val Ile Asp Ile Tyr Glu Tyr
                100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Leu Met Ala Phe Asp Ile Glu Thr
130                 135                 140

Phe Tyr His Glu Gly Asp Glu Phe Gly Lys Gly Glu Ile Ile Met Ile
145                 150                 155                 160

Ser Tyr Ala Asp Glu Glu Ala Arg Val Ile Thr Trp Lys Asn Ile
            165                 170                 175

Asp Leu Pro Tyr Val Asp Val Ser Asn Glu Arg Glu Met Ile Lys
            180                 185                 190

Arg Phe Val Gln Ile Val Arg Glu Lys Asp Pro Asp Val Leu Ile Thr
    195                 200                 205

Tyr Asn Gly Asp Asn Phe Asp Leu Pro Tyr Leu Ile Lys Arg Ala Glu
    210                 215                 220

Lys Leu Gly Val Thr Leu Leu Gly Arg Asp Lys Glu His Pro Glu
225                 230                 235                 240

Pro Lys Ile His Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Glu Arg Asn Glu
        355                 360                 365

Leu Ala Pro Asn Lys Pro Asp Glu Glu Glu Tyr Arg Arg Arg Leu Arg
370                 375                 380

Thr Thr Tyr Leu Gly Gly Tyr Val Lys Glu Pro Glu Arg Gly Leu Trp
385                 390                 395                 400

Glu Asn Ile Thr Tyr Leu Asp Phe Arg Cys Leu Tyr Pro Ser Ile Ile
                405                 410                 415

Val Thr His Asn Val Ser Pro Asp Thr Leu Glu Arg Glu Gly Cys Lys
            420                 425                 430

Asn Tyr Asp Val Ala Pro Ile Val Gly Tyr Lys Phe Cys Lys Asp Phe
        435                 440                 445

Pro Gly Phe Ile Pro Ser Ile Leu Gly Glu Leu Ile Thr Met Arg Gln
    450                 455                 460

Glu Ile Lys Lys Lys Met Lys Ala Thr Ile Asp Pro Ile Glu Lys Lys
465                 470                 475                 480

Met Leu Asp Tyr Arg Gln Arg Ala Val Lys Leu His Ala Asn Ser Tyr
                485                 490                 495

Tyr Gly Tyr Met Gly Tyr Pro Lys Ala Arg Trp Tyr Ser Lys Glu Cys
```

```
                    500             505             510
Ala Glu Ser Val Thr Ala Trp Gly Arg His Tyr Ile Glu Met Thr Ile
        515                 520                 525

Lys Glu Ile Glu Glu Lys Phe Gly Phe Lys Val Leu Tyr Ala Asp Thr
        530                 535                 540

Asp Gly Phe Tyr Ala Thr Ile Pro Gly Glu Lys Pro Glu Thr Ile Lys
545                 550                 555                 560

Lys Lys Ala Lys Glu Phe Leu Lys Tyr Ile Asn Ser Lys Leu Pro Gly
                565                 570                 575

Leu Leu Glu Leu Glu Tyr Glu Gly Phe Tyr Leu Arg Gly Phe Phe Val
        580                 585                 590

Ala Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
        610                 615                 620

Thr Gln Ala Lys Val Leu Glu Ala Ile Leu Lys Glu Asp Ser Val Glu
625                 630                 635                 640

Lys Ala Val Glu Ile Val Lys Asp Val Val Glu Glu Ile Ala Lys Tyr
                645                 650                 655

Gln Val Pro Leu Glu Lys Leu Val Ile His Glu Gln Ile Thr Lys Asp
                660                 665                 670

Leu Ser Glu Tyr Lys Ala Ile Gly Pro His Val Ala Ile Ala Lys Arg
        675                 680                 685

Leu Ala Ala Lys Gly Ile Lys Val Arg Pro Gly Thr Ile Ile Ser Tyr
        690                 695                 700

Ile Val Leu Arg Gly Ser Gly Lys Ile Ser Asp Arg Val Ile Leu Leu
705                 710                 715                 720

Ser Glu Tyr Asp Pro Lys Lys His Lys Tyr Asp Pro Asp Tyr Tyr Ile
                725                 730                 735

Glu Asn Gln Val Leu Pro Ala Val Leu Arg Ile Leu Glu Ala Phe Gly
                740                 745                 750

Tyr Arg Lys Glu Asp Leu Lys Tyr Gln Ser Ser Lys Gln Val Gly Leu
        755                 760                 765

Asp Ala Trp Leu Lys Lys
770
```